US011819474B2

(12) United States Patent
Hertenstein et al.

(10) Patent No.: US 11,819,474 B2
(45) Date of Patent: Nov. 21, 2023

(54) HAIR CARE COMPOSITIONS COMPRISING MALODOR REDUCTION MATERIALS

(71) Applicant: The Procter & Gamble Company, Cincinnati, OH (US)

(72) Inventors: Stacy Renee Hertenstein, Mason, OH (US); Jianjun Justin Li, West Chester, OH (US); Mara O'Brien Gannatti, Cincinnati, OH (US); Jennifer Anne Corder, West Chester Township, OH (US); Steven Louis Diersing, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/541,547

(22) Filed: Dec. 3, 2021

(65) Prior Publication Data
US 2022/0175640 A1 Jun. 9, 2022

Related U.S. Application Data

(60) Provisional application No. 63/121,462, filed on Dec. 4, 2020.

(51) Int. Cl.
A61Q 5/02 (2006.01)
A61Q 5/12 (2006.01)
A61K 8/31 (2006.01)
A61K 8/9789 (2017.01)

(52) U.S. Cl.
CPC ............ A61K 8/31 (2013.01); A61K 8/9789 (2017.08); A61Q 5/02 (2013.01); A61Q 5/12 (2013.01)

(58) Field of Classification Search
None
See application file for complete search history.

(56) References Cited

U.S. PATENT DOCUMENTS

| | | |
|---|---|---|
| 1,489,388 A | 4/1924 | Glenn |
| 1,600,340 A | 9/1926 | Hoffman |
| 1,612,255 A | 12/1926 | Borreca |
| 2,438,091 A | 3/1948 | Lynch |
| 2,528,378 A | 10/1950 | Mannheimer |
| 2,658,072 A | 11/1953 | Milton |
| 2,809,971 A | 10/1957 | Jack et al. |
| 2,879,231 A | 3/1959 | Marshall |
| 3,219,656 A | 11/1965 | Boettner |
| 3,236,733 A | 2/1966 | Karsten et al. |
| 3,373,208 A | 3/1968 | Blumenthal |
| 3,636,113 A | 1/1972 | Hall |
| 3,709,437 A | 1/1973 | Wright |
| 3,716,498 A | 2/1973 | Hall |
| 3,753,196 A | 8/1973 | Kurtz et al. |
| 3,761,418 A | 9/1973 | Parran |
| 3,792,068 A | 2/1974 | Luedders et al. |
| 3,887,692 A | 6/1975 | Gilman |
| 3,904,741 A | 9/1975 | Jones et al. |
| 3,950,532 A | 4/1976 | Bouillon et al. |
| 3,959,160 A | 5/1976 | Horsler et al. |
| 4,049,792 A | 9/1977 | Elsnau |
| 4,089,945 A * | 5/1978 | Brinkman ............... A61Q 5/006 510/508 |
| 4,120,948 A | 10/1978 | Shelton |
| 4,137,180 A | 1/1979 | Naik |
| 4,237,155 A | 12/1980 | Kardouche |
| 4,309,119 A | 1/1982 | Wittersheim |
| 4,323,683 A | 4/1982 | Bolich, Jr. et al. |
| 4,329,334 A | 5/1982 | Su et al. |
| 4,345,080 A | 8/1982 | Bolich, Jr. |
| 4,359,456 A | 11/1982 | Gosling et al. |
| 4,379,753 A | 4/1983 | Bolich, Jr. |
| 4,430,243 A | 2/1984 | Bragg |
| 4,470,982 A | 9/1984 | Winkler |
| 4,726,945 A | 2/1988 | Patel |
| 4,732,696 A | 3/1988 | Urfer |
| 4,839,166 A | 6/1989 | Grollier et al. |
| 4,854,333 A | 8/1989 | Inman et al. |
| 4,867,971 A | 9/1989 | Ryan et al. |
| 4,931,274 A | 6/1990 | Barabino et al. |
| 4,973,416 A | 11/1990 | Kennedy |
| 4,985,238 A | 1/1991 | Tanner et al. |
| 4,997,641 A | 3/1991 | Hartnett |

(Continued)

FOREIGN PATENT DOCUMENTS

| | | |
|---|---|---|
| BE | 825146 A | 8/1975 |
| CA | 704195 A | 2/1965 |

(Continued)

OTHER PUBLICATIONS

Air Quality of the Iowa Department of Natural Resources. A Review of the Science and Technology of Odor Measurement, 2005, 51 pages (2005).
All Office Actions; U.S. Appl. No. 14/865,048, filed Sep. 25, 2015.
All Office Actions; U.S. Appl. No. 14/865,257, filed Sep. 25, 2015.
All Office Actions; U.S. Appl. No. 15/467,331, filed Mar. 23, 2017.
All Office Actions; U.S. Appl. No. 15/597,391, filed May 17, 2017.
All Office Actions; U.S. Appl. No. 15/597,376, filed May 17, 2017.
All Office Actions; U.S. Appl. No. 15/708,205, filed Sep. 19, 2017.
All Office Actions; U.S. Appl. No. 16/810,222, filed Mar. 5, 2020.
All Office Actions; U.S. Appl. No. 16/810,207, filed Mar. 4, 2020.
All Office Actions; U.S. Appl. No. 17/111,906, filed Dec. 4, 2020.
All Office Actions; U.S. Appl. No. 17/111,919, filed Dec. 4, 2020.

(Continued)

Primary Examiner — Jyothsna A Venkat
(74) Attorney, Agent, or Firm — Linda M. Sivik

(57) ABSTRACT

The present invention discloses a hair care composition comprising, based on total composition weight, a) a sum total of from about 0.1% to about 2% of a perfume with one or more malodor reduction materials having a wt % from about 0.0001% to about 2% of one or more of said malodor reduction materials; b) from about 0.01% to about 10% of a scalp active material selected from the group consisting of sulfur and mixtures thereof; c) from about 0.1% to about 40% of a surfactant.

11 Claims, No Drawings

(56) References Cited

U.S. PATENT DOCUMENTS

| | | |
|---|---|---|
| 5,019,375 A | 5/1991 | Tanner et al. |
| 5,093,112 A | 3/1992 | Birtwistle et al. |
| 5,104,646 A | 4/1992 | Bolich, Jr. |
| 5,106,609 A | 4/1992 | Bolich, Jr. |
| 5,135,747 A | 8/1992 | Faryniarz et al. |
| 5,156,834 A | 10/1992 | Beckmeyer et al. |
| 5,294,644 A | 3/1994 | Login et al. |
| 5,296,622 A | 3/1994 | Uphues |
| 5,298,640 A | 3/1994 | Callaghan et al. |
| 5,332,569 A | 7/1994 | Wood et al. |
| 5,364,031 A | 11/1994 | Taniguchi et al. |
| 5,374,421 A | 12/1994 | Tashiro |
| 5,374,614 A | 12/1994 | Behan et al. |
| 5,409,695 A | 4/1995 | Abrutyn et al. |
| 5,415,810 A | 5/1995 | Lee et al. |
| 5,417,965 A | 5/1995 | Janchitraponvej et al. |
| 5,429,816 A | 7/1995 | Hofrichter et al. |
| 5,439,682 A | 8/1995 | Wivell |
| 5,441,659 A | 8/1995 | Minor |
| 5,486,303 A | 1/1996 | Capeci |
| 5,489,392 A | 2/1996 | Capeci |
| 5,516,448 A | 5/1996 | Capeci |
| 5,536,493 A | 7/1996 | Dubief |
| 5,554,588 A | 9/1996 | Behan et al. |
| 5,560,918 A | 10/1996 | Wivell |
| 5,565,422 A | 10/1996 | Del Greco |
| 5,569,645 A | 10/1996 | Dinniwell |
| 5,574,005 A | 11/1996 | Welch |
| 5,576,282 A | 11/1996 | Miracle |
| 5,578,298 A | 11/1996 | Berthiaume |
| 5,595,967 A | 1/1997 | Miracle |
| 5,597,936 A | 1/1997 | Perkins |
| 5,599,549 A | 2/1997 | Wivell |
| 5,624,666 A | 4/1997 | Coffindaffer et al. |
| 5,635,469 A | 6/1997 | Fowler et al. |
| 5,665,267 A | 9/1997 | Dowell et al. |
| 5,691,297 A | 11/1997 | Nassano |
| 5,714,137 A | 2/1998 | Trinh |
| 5,747,436 A | 5/1998 | Patel |
| 5,776,444 A | 7/1998 | Birtwistle et al. |
| 5,800,897 A | 9/1998 | Sharma |
| 5,816,446 A | 10/1998 | Steindorf et al. |
| 5,830,440 A | 11/1998 | Sturla et al. |
| 5,853,618 A | 12/1998 | Barker |
| 5,879,584 A | 3/1999 | Bianchetti |
| 5,891,424 A | 4/1999 | Bretzler et al. |
| 5,902,225 A | 5/1999 | Monson |
| 5,925,603 A | 7/1999 | D Angelo |
| 5,942,217 A | 8/1999 | Woo et al. |
| 5,976,514 A | 11/1999 | Guskey et al. |
| 5,980,877 A | 11/1999 | Baravetto |
| 5,985,939 A | 11/1999 | Minor |
| 6,015,547 A | 1/2000 | Yam |
| 6,015,780 A | 1/2000 | Llosas Bigorra et al. |
| 6,020,303 A | 2/2000 | Cripe et al. |
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,139,828 A | 10/2000 | Mccullough |
| 6,153,567 A | 11/2000 | Hughes |
| 6,153,569 A | 11/2000 | Halloran |
| 6,162,834 A | 12/2000 | Sebillotte-Arnaud et al. |
| 6,180,121 B1 | 1/2001 | Guenin et al. |
| 6,225,464 B1 | 5/2001 | Hiler, II |
| 6,231,844 B1 | 5/2001 | Nambu |
| 6,232,302 B1 | 5/2001 | Alberico et al. |
| 6,248,135 B1 | 6/2001 | Trinh et al. |
| 6,268,431 B1 | 7/2001 | Snyder et al. |
| 6,284,225 B1 | 9/2001 | Bhatt |
| 6,329,331 B1 | 12/2001 | Aronson |
| 6,335,312 B1 | 1/2002 | Coffindaffer et al. |
| 6,352,688 B1 | 3/2002 | Scavone et al. |
| 6,386,392 B1 | 5/2002 | Argentieri |
| 6,413,920 B1 | 7/2002 | Bettiol |
| 6,423,305 B1 | 7/2002 | Cauwet-Martin et al. |
| 6,436,442 B1 | 8/2002 | Woo et al. |
| 6,451,300 B1 | 9/2002 | Dunlop et al. |
| 6,488,943 B1 | 12/2002 | Beerse et al. |
| 6,511,669 B1 | 1/2003 | Garnier et al. |
| 6,565,863 B1 | 5/2003 | Guillou et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop et al. |
| 6,656,923 B1 | 12/2003 | Trinh |
| 6,660,288 B1 | 12/2003 | Behan et al. |
| 6,679,324 B2 | 1/2004 | Den Boer et al. |
| 6,716,455 B2 | 4/2004 | Birkel |
| 6,716,805 B1 | 4/2004 | Sherry |
| 6,740,713 B1 | 5/2004 | Busch et al. |
| 6,743,760 B1 | 6/2004 | Hardy et al. |
| 6,764,986 B1 | 7/2004 | Busch et al. |
| 6,767,507 B1 | 7/2004 | Woo et al. |
| 6,794,356 B2 | 9/2004 | Turner |
| 6,814,088 B2 | 11/2004 | Barnabas et al. |
| 6,827,795 B1 | 12/2004 | Kasturi et al. |
| 6,869,923 B1 | 3/2005 | Cunningham |
| 6,897,253 B2 | 5/2005 | Schmucker-castner |
| 6,908,889 B2 | 6/2005 | Niemiec et al. |
| 6,930,078 B2 | 8/2005 | Wells |
| 6,992,054 B2 | 1/2006 | Lee et al. |
| 7,018,978 B2 | 3/2006 | Miracle et al. |
| 7,030,068 B2 | 4/2006 | Clare et al. |
| 7,100,767 B2 | 9/2006 | Chomik et al. |
| 7,151,079 B2 | 12/2006 | Fack et al. |
| 7,172,099 B2 | 2/2007 | Hoefte |
| 7,202,198 B2 | 4/2007 | Gordon et al. |
| 7,217,752 B2 | 5/2007 | Schmucker-Castner et al. |
| 7,220,408 B2 | 5/2007 | Decoster et al. |
| 7,223,361 B2 | 5/2007 | Kvietok |
| 7,223,385 B2 | 5/2007 | Gawtrey et al. |
| 7,485,289 B2 | 2/2009 | Gawtrey et al. |
| 7,504,094 B2 | 3/2009 | Decoster et al. |
| 7,531,497 B2 | 5/2009 | Midha et al. |
| 7,541,320 B2 | 6/2009 | Dabkowski et al. |
| 7,598,213 B2 | 10/2009 | Geary et al. |
| 7,659,233 B2 | 2/2010 | Hurley et al. |
| 7,666,825 B2 | 2/2010 | Wagner et al. |
| 7,820,609 B2 | 10/2010 | Soffin et al. |
| 7,829,514 B2 | 11/2010 | Paul et al. |
| 7,841,036 B2 | 11/2010 | Smith |
| 7,867,505 B2 | 1/2011 | Elliott et al. |
| 7,928,053 B2 | 4/2011 | Hecht et al. |
| 7,977,288 B2 | 7/2011 | SenGupta |
| 8,007,545 B2 | 8/2011 | Fujii et al. |
| 8,058,500 B2 | 11/2011 | Sojka et al. |
| 8,084,407 B2 | 12/2011 | Soffin et al. |
| 8,088,721 B2 | 1/2012 | Soffin et al. |
| 8,119,168 B2 | 2/2012 | Johnson |
| 8,124,063 B2 | 2/2012 | Harichian et al. |
| 8,158,571 B2 | 4/2012 | Alonso |
| 8,300,949 B2 | 10/2012 | Xu |
| 8,322,631 B2 | 12/2012 | Richardson et al. |
| 8,343,469 B2 | 1/2013 | Bierganns et al. |
| 8,349,300 B2 | 1/2013 | Wells |
| 8,357,359 B2 | 1/2013 | Woo et al. |
| 8,361,450 B2 | 1/2013 | Johnson et al. |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,491,877 B2 | 7/2013 | Schwartz et al. |
| 8,539,631 B2 | 9/2013 | Catalfamo et al. |
| 8,574,561 B2 | 11/2013 | Patel et al. |
| 8,580,725 B2 | 11/2013 | Kuhlman et al. |
| 8,609,600 B2 | 12/2013 | Warr et al. |
| 8,628,760 B2 | 1/2014 | Carter et al. |
| 8,629,095 B2 | 1/2014 | Deleersnyder |
| 8,653,014 B2 | 2/2014 | Hilvert |
| 8,675,919 B2 | 3/2014 | Maladen |
| 8,679,316 B2 | 3/2014 | Brunner et al. |

(56) References Cited

U.S. PATENT DOCUMENTS

| | | |
|---|---|---|
| 8,680,035 B2 | 3/2014 | Kuhlman et al. |
| 8,699,751 B2 | 4/2014 | Maladen |
| 8,709,337 B2 | 4/2014 | Gruenbacher et al. |
| 8,709,385 B2 | 4/2014 | Tamarkin |
| 8,741,275 B2 | 6/2014 | Dente et al. |
| 8,741,363 B2 | 6/2014 | Albrecht et al. |
| 8,771,765 B1 | 7/2014 | Fernandez |
| 8,772,354 B2 | 7/2014 | Williams et al. |
| 8,795,635 B2 | 8/2014 | Tamarkin et al. |
| 8,877,316 B2 | 11/2014 | Hasenoehrl et al. |
| 8,883,698 B2 | 11/2014 | Scheibel et al. |
| 8,931,711 B2 | 1/2015 | Gruenbacher |
| 8,980,239 B2 | 3/2015 | Staudigel et al. |
| 8,987,187 B2 | 3/2015 | Smets et al. |
| 9,006,162 B1 | 4/2015 | Rizk |
| 9,186,642 B2 | 11/2015 | Dihora et al. |
| 9,187,407 B2 | 11/2015 | Koshti et al. |
| 9,265,727 B1 | 2/2016 | Lowenborg |
| 9,272,164 B2 | 3/2016 | Johnson et al. |
| 9,296,550 B2 | 3/2016 | Smith |
| 9,308,398 B2 | 4/2016 | Hutton et al. |
| 9,393,447 B2 | 7/2016 | Zasloff |
| 9,428,616 B2 | 8/2016 | Wagner |
| 9,512,275 B2 | 12/2016 | Wagner |
| 9,610,239 B2 | 4/2017 | Feng |
| 9,655,821 B2 | 5/2017 | Carter et al. |
| 9,662,291 B2 | 5/2017 | Johnson et al. |
| 9,682,021 B2 | 6/2017 | Tamarkin et al. |
| 9,776,787 B2 | 10/2017 | Nakajima |
| 9,949,901 B2 | 4/2018 | Zhao et al. |
| 9,949,911 B2 | 4/2018 | Cetti |
| 9,968,535 B2 | 5/2018 | Kitko |
| 9,968,537 B2 | 5/2018 | Sharma |
| 9,993,419 B2 | 6/2018 | Glenn, Jr. |
| 9,993,420 B2 | 6/2018 | Glenn, Jr. et al. |
| 10,039,706 B2 | 8/2018 | Meralli et al. |
| 10,039,939 B2 | 8/2018 | Xavier et al. |
| 10,113,140 B2 | 10/2018 | Frankenbach |
| 10,182,976 B2 | 1/2019 | Staudigel |
| 10,238,685 B2 | 3/2019 | Dunn et al. |
| 10,265,261 B2 | 4/2019 | Park et al. |
| 10,311,575 B2 | 6/2019 | Stofel |
| 10,392,625 B2 | 8/2019 | Jin et al. |
| 10,426,713 B2 | 10/2019 | Song |
| 10,441,519 B2 | 10/2019 | Zhao |
| 10,552,557 B2 | 2/2020 | Frankenbach et al. |
| 10,610,473 B2 | 4/2020 | Hertenstein et al. |
| 10,653,590 B2 | 5/2020 | Torres Rivera |
| 10,799,434 B2 | 10/2020 | Torres Rivera |
| 10,842,720 B2 | 11/2020 | Thompson |
| 10,881,597 B2 | 1/2021 | Lane et al. |
| 10,888,505 B2 | 1/2021 | Johnson |
| 10,912,732 B2 | 2/2021 | Gillis |
| 11,116,703 B2 | 9/2021 | Song et al. |
| 11,116,704 B2 | 9/2021 | Song et al. |
| 11,129,775 B2 | 9/2021 | Song et al. |
| 11,334,694 B2 | 5/2022 | Cetti et al. |
| 11,334,695 B2 | 5/2022 | Cetti et al. |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0012646 A1 | 1/2002 | Royce et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0003070 A1 | 1/2003 | Eggers et al. |
| 2003/0008787 A1 | 1/2003 | Mcgee et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0083210 A1 | 5/2003 | Goldberg |
| 2003/0108501 A1 | 6/2003 | Hofrichter |
| 2003/0147842 A1 | 8/2003 | Restle et al. |
| 2003/0154561 A1 | 8/2003 | Patel |
| 2003/0161802 A1 | 8/2003 | Flammer |
| 2003/0180238 A1 | 9/2003 | Sakurai et al. |
| 2003/0180246 A1 | 9/2003 | Frantz et al. |
| 2003/0185867 A1 | 10/2003 | Kerschner et al. |
| 2003/0192922 A1 | 10/2003 | Ceppaluni et al. |
| 2003/0202952 A1 | 10/2003 | Wells et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0064117 A1 | 4/2004 | Hammons |
| 2004/0144863 A1 | 7/2004 | Kendrick |
| 2004/0151793 A1 | 8/2004 | Paspaleeva-kuhn et al. |
| 2004/0157754 A1 | 8/2004 | Geary et al. |
| 2004/0229963 A1 | 11/2004 | Stephane |
| 2004/0234484 A1 | 11/2004 | Peffly |
| 2004/0235689 A1 | 11/2004 | Sakai et al. |
| 2005/0003975 A1 | 1/2005 | Browne et al. |
| 2005/0003980 A1 | 1/2005 | Baker |
| 2005/0020468 A1 | 1/2005 | Frantz et al. |
| 2005/0136011 A1 | 6/2005 | Nekludoff |
| 2005/0152863 A1 | 7/2005 | Brautigam |
| 2005/0192207 A1 | 9/2005 | Morgan, III et al. |
| 2005/0201967 A1 | 9/2005 | Albrecht et al. |
| 2005/0202984 A1 | 9/2005 | Schwartz et al. |
| 2005/0227902 A1 | 10/2005 | Erazo-majewicz et al. |
| 2005/0233929 A1 | 10/2005 | Queen |
| 2005/0245407 A1 | 11/2005 | Ishihara |
| 2005/0276831 A1 | 12/2005 | Dihora |
| 2006/0002880 A1 | 1/2006 | Peffly |
| 2006/0005333 A1 | 1/2006 | Catalfamo et al. |
| 2006/0009337 A1 | 1/2006 | Smith |
| 2006/0030509 A1 | 2/2006 | Modi |
| 2006/0034778 A1 | 2/2006 | Kitano et al. |
| 2006/0057075 A1 | 3/2006 | Arkin et al. |
| 2006/0057097 A1 | 3/2006 | Derici |
| 2006/0079417 A1 | 4/2006 | Wagner |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0084589 A1 | 4/2006 | Vlad et al. |
| 2006/0090777 A1 | 5/2006 | Hecht et al. |
| 2006/0094610 A1 | 5/2006 | Yamato et al. |
| 2006/0110415 A1 | 5/2006 | Gupta |
| 2006/0120982 A1 | 6/2006 | Derici et al. |
| 2006/0120988 A1 | 6/2006 | Bailey et al. |
| 2006/0135397 A1 | 6/2006 | Bissey-beugras |
| 2006/0166857 A1 | 7/2006 | Surburg et al. |
| 2006/0171911 A1 | 8/2006 | Schwartz et al. |
| 2006/0183662 A1 | 8/2006 | Crotty |
| 2006/0210139 A1 | 9/2006 | Carroll |
| 2006/0229227 A1 | 10/2006 | Goldman |
| 2006/0252662 A1 | 11/2006 | Soffin |
| 2006/0263319 A1 | 11/2006 | Fan et al. |
| 2006/0276357 A1 | 12/2006 | Smith, III et al. |
| 2006/0292104 A1 | 12/2006 | Guskey |
| 2007/0003499 A1 | 1/2007 | Shen et al. |
| 2007/0020263 A1 | 1/2007 | Shitara et al. |
| 2007/0072781 A1 | 3/2007 | Soffin et al. |
| 2007/0110700 A1 | 5/2007 | Wells |
| 2007/0154402 A1 | 7/2007 | Trumbore et al. |
| 2007/0155637 A1 | 7/2007 | Smith, III et al. |
| 2007/0160555 A1 | 7/2007 | Staudigel |
| 2007/0179207 A1 | 8/2007 | Fernandez de Castro et al. |
| 2007/0225193 A1 | 9/2007 | Kuhlman et al. |
| 2007/0269397 A1 | 11/2007 | Terada |
| 2007/0275866 A1 | 11/2007 | Dykstra |
| 2007/0292380 A1 | 12/2007 | Staudigel |
| 2007/0298994 A1 | 12/2007 | Finke et al. |
| 2008/0003245 A1 | 1/2008 | Kroepke et al. |
| 2008/0008668 A1 | 1/2008 | Harichian et al. |
| 2008/0019928 A1 | 1/2008 | Franzke |
| 2008/0063618 A1 | 3/2008 | Johnson |
| 2008/0138442 A1 | 6/2008 | Johnson |
| 2008/0152610 A1 | 6/2008 | Cajan |
| 2008/0160093 A1 | 7/2008 | Schwartz et al. |

(56) References Cited

U.S. PATENT DOCUMENTS

| | | |
|---|---|---|
| 2008/0176780 A1 | 7/2008 | Warr |
| 2008/0194454 A1 | 8/2008 | Morgan |
| 2008/0206179 A1 | 8/2008 | Peffly et al. |
| 2008/0260655 A1 | 10/2008 | Tamarkin et al. |
| 2008/0260665 A1 | 10/2008 | Guerchet et al. |
| 2008/0261844 A1 | 10/2008 | Ruppert et al. |
| 2008/0317698 A1 | 12/2008 | Wells et al. |
| 2009/0005280 A1 | 1/2009 | Woo et al. |
| 2009/0029900 A1 | 1/2009 | Cetti et al. |
| 2009/0041702 A1 | 2/2009 | Molenda |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0197784 A1 | 8/2009 | Ainger |
| 2009/0221463 A1 | 9/2009 | Kitko et al. |
| 2009/0240223 A1 | 9/2009 | Warren |
| 2009/0246236 A1 | 10/2009 | Kitko |
| 2009/0312223 A1 | 12/2009 | Yang et al. |
| 2009/0312224 A1 | 12/2009 | Yang et al. |
| 2009/0324505 A1 | 12/2009 | Seidling |
| 2010/0000116 A1 | 1/2010 | Aouad et al. |
| 2010/0001116 A1 | 1/2010 | Johnson |
| 2010/0009285 A1 | 1/2010 | Daems et al. |
| 2010/0061946 A1 | 3/2010 | Scherner et al. |
| 2010/0087357 A1 | 4/2010 | Morgan, III et al. |
| 2010/0152083 A1 | 6/2010 | Velazquez |
| 2010/0168251 A1 | 7/2010 | Warr et al. |
| 2010/0183539 A1 | 7/2010 | Bernhardt |
| 2010/0215775 A1 | 8/2010 | Schmaus et al. |
| 2010/0287710 A1 | 11/2010 | Denutte et al. |
| 2010/0310644 A1 | 12/2010 | Liebmann |
| 2010/0322878 A1 | 12/2010 | Stella et al. |
| 2011/0008267 A1 | 1/2011 | Arkin et al. |
| 2011/0023266 A1 | 2/2011 | Gross et al. |
| 2011/0098209 A1 | 4/2011 | Smets et al. |
| 2011/0107524 A1 | 5/2011 | Chieffi et al. |
| 2011/0118691 A1 | 5/2011 | Nishitani |
| 2011/0139170 A1 | 6/2011 | Hippe et al. |
| 2011/0150815 A1 | 6/2011 | Woo et al. |
| 2011/0165107 A1 | 7/2011 | Derks et al. |
| 2011/0171155 A1 | 7/2011 | Federle |
| 2011/0177017 A1 | 7/2011 | Coffindaffer et al. |
| 2011/0232668 A1 | 9/2011 | Hoffmann et al. |
| 2011/0245126 A1 | 10/2011 | Tsaur et al. |
| 2011/0245134 A1 | 10/2011 | Smets |
| 2011/0245136 A1 | 10/2011 | Smets |
| 2011/0268778 A1 | 11/2011 | Dihora et al. |
| 2011/0269657 A1 | 11/2011 | Dihora et al. |
| 2011/0300095 A1 | 12/2011 | Dente et al. |
| 2011/0303766 A1 | 12/2011 | Smith |
| 2011/0305739 A1 | 12/2011 | Royce |
| 2011/0305778 A1 | 12/2011 | Caggioni et al. |
| 2011/0308555 A1 | 12/2011 | Smets et al. |
| 2011/0308556 A1 | 12/2011 | Smets et al. |
| 2011/0319790 A1 | 12/2011 | Kost et al. |
| 2012/0004328 A1 | 1/2012 | Huchel et al. |
| 2012/0009285 A1 | 1/2012 | Wei et al. |
| 2012/0014901 A1 | 1/2012 | Sunkel et al. |
| 2012/0031419 A1 | 2/2012 | Batt |
| 2012/0034173 A1 | 2/2012 | Batt |
| 2012/0052031 A1 | 3/2012 | Troccaz et al. |
| 2012/0100091 A1 | 4/2012 | Hata et al. |
| 2012/0100092 A1 | 4/2012 | Murray |
| 2012/0129924 A1 | 5/2012 | Park et al. |
| 2012/0219610 A1 | 8/2012 | Smith, III et al. |
| 2012/0230936 A1 | 9/2012 | Mikkelsen |
| 2012/0237469 A1 | 9/2012 | Dente et al. |
| 2012/0246851 A1 | 10/2012 | Smith, III et al. |
| 2012/0258150 A1 | 10/2012 | Rauckhorst et al. |
| 2012/0291911 A1 | 11/2012 | Smith |
| 2012/0309660 A1 | 12/2012 | Kawasoe |
| 2012/0316095 A1 | 12/2012 | Wei et al. |
| 2013/0029932 A1 | 1/2013 | Kachi et al. |
| 2013/0034515 A1 | 2/2013 | Stone et al. |
| 2013/0043145 A1 | 2/2013 | Smith, III et al. |
| 2013/0043146 A1 | 2/2013 | Smith, III et al. |
| 2013/0043147 A1 | 2/2013 | Smith, III et al. |
| 2013/0045285 A1 | 2/2013 | Stella et al. |
| 2013/0053295 A1 | 2/2013 | Kinoshita et al. |
| 2013/0053300 A1 | 2/2013 | Scheibel et al. |
| 2013/0089587 A1 | 4/2013 | Staudigel |
| 2013/0115173 A1 | 5/2013 | Trumbore et al. |
| 2013/0136713 A1 | 5/2013 | Terada et al. |
| 2013/0143784 A1 | 6/2013 | Rizk |
| 2013/0150338 A1 | 6/2013 | Ananthapadmanabhan |
| 2013/0156712 A1 | 6/2013 | Frantz |
| 2013/0189212 A1 | 7/2013 | Jawale et al. |
| 2013/0211952 A1 | 8/2013 | Sugaya |
| 2013/0216491 A1 | 8/2013 | Ogihara et al. |
| 2013/0243718 A1 | 9/2013 | Pasquet |
| 2013/0244922 A1 | 9/2013 | Bartelt |
| 2013/0266642 A1 | 10/2013 | Hollingshead et al. |
| 2013/0280192 A1 | 10/2013 | Carter et al. |
| 2013/0280202 A1 | 10/2013 | Stella et al. |
| 2013/0284195 A1 | 10/2013 | Murdock |
| 2013/0296289 A1 | 11/2013 | Hall et al. |
| 2013/0319463 A1 | 12/2013 | Policicchio |
| 2014/0037703 A1 | 2/2014 | Dihora et al. |
| 2014/0039066 A1 | 2/2014 | Grimadell et al. |
| 2014/0086893 A1 | 3/2014 | Gutmann et al. |
| 2014/0112879 A1 | 4/2014 | Molenda et al. |
| 2014/0127149 A1 | 5/2014 | Lepilleur |
| 2014/0131395 A1 | 5/2014 | Chang |
| 2014/0134125 A1 | 5/2014 | Dahl |
| 2014/0162979 A1 | 6/2014 | Palla-venkata |
| 2014/0171471 A1 | 6/2014 | Krueger |
| 2014/0186864 A1 | 7/2014 | Kato et al. |
| 2014/0201927 A1 | 7/2014 | Bianchetti et al. |
| 2014/0216495 A1 | 8/2014 | Bureiko |
| 2014/0221269 A1 | 8/2014 | Sobel et al. |
| 2014/0228268 A1 | 8/2014 | Fahl et al. |
| 2014/0237732 A1 | 8/2014 | Zuedel Fernandes et al. |
| 2014/0246515 A1 | 9/2014 | Nakajima |
| 2014/0308227 A1 | 10/2014 | Mabille |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2014/0349902 A1 | 11/2014 | Allef et al. |
| 2015/0017152 A1 | 1/2015 | Potechin et al. |
| 2015/0021496 A1 | 1/2015 | Shabbir |
| 2015/0037273 A1 | 2/2015 | Wagner |
| 2015/0050231 A1 | 2/2015 | Murase |
| 2015/0071977 A1 | 3/2015 | Dihora |
| 2015/0093420 A1 | 4/2015 | Snyder |
| 2015/0093429 A1 | 4/2015 | Carter et al. |
| 2015/0098921 A1 | 4/2015 | Franzke et al. |
| 2015/0099684 A1 | 4/2015 | Boutique |
| 2015/0108163 A1 | 4/2015 | Smith et al. |
| 2015/0110728 A1 | 4/2015 | Jayaswal |
| 2015/0141310 A1 | 5/2015 | Smets et al. |
| 2015/0147286 A1 | 5/2015 | Barrera |
| 2015/0157548 A1 | 6/2015 | De Feij et al. |
| 2015/0218496 A1 | 8/2015 | Schmiedel et al. |
| 2015/0231045 A1 | 8/2015 | Krohn et al. |
| 2015/0262354 A1 | 9/2015 | Periaswamy |
| 2015/0297489 A1 | 10/2015 | Kleinen et al. |
| 2015/0299400 A1 | 10/2015 | Wagner et al. |
| 2015/0313818 A1 | 11/2015 | Stagg |
| 2015/0352027 A1 | 12/2015 | Thomas et al. |
| 2015/0359725 A1 | 12/2015 | Glenn, Jr. et al. |
| 2015/0359726 A1 | 12/2015 | Glenn, Jr. et al. |
| 2015/0359728 A1 | 12/2015 | Glenn, Jr. et al. |
| 2016/0008257 A1 | 1/2016 | Zhou et al. |
| 2016/0022566 A1 | 1/2016 | Figura |
| 2016/0089317 A1 | 3/2016 | Cetti et al. |
| 2016/0089318 A1 | 3/2016 | Cetti et al. |
| 2016/0089322 A1 | 3/2016 | Santos Nogueira et al. |
| 2016/0089462 A1 | 3/2016 | Frankenbach |
| 2016/0089464 A1 | 3/2016 | Frankenbach et al. |
| 2016/0089465 A1 | 3/2016 | Frankenbach et al. |
| 2016/0090555 A1 | 3/2016 | Frankenbach |
| 2016/0090556 A1 | 3/2016 | Frankenbach et al. |
| 2016/0090557 A1 | 3/2016 | Frankenbach et al. |

(56) References Cited

U.S. PATENT DOCUMENTS

| | | |
|---|---|---|
| 2016/0090558 A1 | 3/2016 | Frankenbach et al. |
| 2016/0092661 A1 | 3/2016 | Hollingshead et al. |
| 2016/0095804 A1 | 4/2016 | Xavier et al. |
| 2016/0113849 A1 | 4/2016 | Grimadell et al. |
| 2016/0128944 A1 | 5/2016 | Chawrai |
| 2016/0193125 A1 | 7/2016 | Jones et al. |
| 2016/0206522 A1 | 7/2016 | Ribaut et al. |
| 2016/0235643 A1 | 8/2016 | Mathonneau et al. |
| 2016/0250115 A1 | 9/2016 | Li et al. |
| 2016/0279048 A1 | 9/2016 | Jayaswal et al. |
| 2016/0287503 A1 | 10/2016 | Schroeder |
| 2016/0287509 A1 | 10/2016 | Peffly |
| 2016/0296656 A1 | 10/2016 | Scavone et al. |
| 2016/0303043 A1 | 10/2016 | Khoury |
| 2016/0306909 A1 | 10/2016 | Hollingshead et al. |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310371 A1 | 10/2016 | Zhao |
| 2016/0310375 A1 | 10/2016 | Torres Rivera |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |
| 2016/0317424 A1 | 11/2016 | Kadir et al. |
| 2016/0326458 A1 | 11/2016 | Smets et al. |
| 2016/0354300 A1 | 12/2016 | Thompson et al. |
| 2017/0066579 A1 | 3/2017 | Zillges |
| 2017/0071837 A1 | 3/2017 | Schelges et al. |
| 2017/0101609 A1 | 4/2017 | Vargas |
| 2017/0110690 A1 | 4/2017 | Lamansky et al. |
| 2017/0110695 A1 | 4/2017 | Nishikawa et al. |
| 2017/0119917 A1 | 5/2017 | Frankenbach et al. |
| 2017/0137752 A1 | 5/2017 | Frankenbach et al. |
| 2017/0137753 A1 | 5/2017 | Frankenbach et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0239155 A1 | 8/2017 | Hartnett |
| 2017/0249407 A1 | 8/2017 | Cetti et al. |
| 2017/0249408 A1 | 8/2017 | Cetti et al. |
| 2017/0252273 A1 | 9/2017 | Renock et al. |
| 2017/0255725 A1 | 9/2017 | Frankenbach et al. |
| 2017/0278249 A1 | 9/2017 | Stofel |
| 2017/0283959 A1 | 10/2017 | Shellef |
| 2017/0304172 A1 | 10/2017 | Chang et al. |
| 2017/0304184 A1 | 10/2017 | Glenn, Jr. |
| 2017/0304185 A1 | 10/2017 | Glenn, Jr. et al. |
| 2017/0304186 A1 | 10/2017 | Glenn, Jr. |
| 2017/0333321 A1 | 11/2017 | Carnali |
| 2017/0333591 A9 | 11/2017 | Scavone et al. |
| 2017/0367963 A1 | 12/2017 | Kadir et al. |
| 2018/0004875 A1 | 1/2018 | Cetti et al. |
| 2018/0044097 A1 | 2/2018 | Zeik |
| 2018/0057451 A1 | 3/2018 | Owens et al. |
| 2018/0066210 A1 | 3/2018 | Frankenbach et al. |
| 2018/0110594 A1 | 4/2018 | Atkin |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson |
| 2018/0110696 A1 | 4/2018 | Johnson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | Park et al. |
| 2018/0116941 A1 | 5/2018 | Wang |
| 2018/0133133 A1 | 5/2018 | Kleinen et al. |
| 2018/0177708 A1 | 6/2018 | Lee et al. |
| 2018/0221266 A1 | 8/2018 | Zhao et al. |
| 2018/0256481 A1 | 9/2018 | Glenn, Jr. |
| 2018/0280270 A1 | 10/2018 | Rughani et al. |
| 2018/0311135 A1 | 11/2018 | Chang |
| 2018/0311136 A1 | 11/2018 | Chang |
| 2018/0318194 A1 | 11/2018 | Hoffmann et al. |
| 2018/0344611 A1 | 12/2018 | Zhao et al. |
| 2018/0344612 A1 | 12/2018 | Zhao et al. |
| 2018/0344613 A1 | 12/2018 | Zhao et al. |
| 2018/0344614 A1 | 12/2018 | Zhao et al. |
| 2018/0360713 A1 | 12/2018 | Jouy et al. |
| 2019/0105242 A1 | 4/2019 | Song |
| 2019/0105243 A1 | 4/2019 | Song |
| 2019/0105244 A1 | 4/2019 | Song |
| 2019/0105245 A1 | 4/2019 | Song |
| 2019/0105246 A1 | 4/2019 | Cochran |
| 2019/0105247 A1 | 4/2019 | Song |
| 2019/0117543 A1 | 4/2019 | Zhao |
| 2019/0117544 A1 | 4/2019 | Zhao |
| 2019/0117545 A1 | 4/2019 | Zhao |
| 2019/0125650 A1 | 5/2019 | Lee et al. |
| 2019/0142711 A1 | 5/2019 | Torres Rivera |
| 2019/0142800 A1 | 5/2019 | Ghosh et al. |
| 2019/0155975 A9 | 5/2019 | Cetti et al. |
| 2019/0167554 A1 | 6/2019 | Wankhade |
| 2019/0183777 A1 | 6/2019 | Gillis |
| 2019/0183778 A1 | 6/2019 | Glenn, Jr. |
| 2019/0192405 A1 | 6/2019 | Zhao |
| 2019/0240121 A1 | 8/2019 | Torres Rivera |
| 2019/0307298 A1 | 10/2019 | Zhao |
| 2019/0328647 A1 | 10/2019 | Chang et al. |
| 2019/0365619 A1 | 12/2019 | Ceballos et al. |
| 2019/0365633 A1 | 12/2019 | Glenn, Jr. |
| 2020/0000690 A1 | 1/2020 | Renock |
| 2020/0078284 A1 | 3/2020 | Botto et al. |
| 2020/0129402 A1 | 4/2020 | Jamadagni |
| 2020/0163846 A1 | 5/2020 | Song |
| 2020/0170894 A1 | 6/2020 | Park et al. |
| 2020/0197272 A1 | 6/2020 | Hertenstein et al. |
| 2020/0206110 A1 | 7/2020 | Hertenstein et al. |
| 2020/0237628 A1 | 7/2020 | Torres Rivera |
| 2021/0022986 A1 | 1/2021 | Glenn, Jr. |
| 2021/0093543 A1 | 4/2021 | Parikh et al. |
| 2021/0121385 A1 | 4/2021 | Muller et al. |
| 2021/0128444 A1 | 5/2021 | Muller et al. |
| 2021/0169765 A1 | 6/2021 | Renock |
| 2021/0212927 A1 | 7/2021 | Hutton, III et al. |
| 2021/0267853 A1 | 9/2021 | Johnson et al. |
| 2021/0275410 A1 | 9/2021 | Hutton, III |
| 2021/0353518 A1 | 11/2021 | Ballhaus et al. |
| 2021/0353522 A1 | 11/2021 | Ballhaus et al. |
| 2021/0401716 A1 | 12/2021 | Gogineni et al. |
| 2022/0160606 A1 | 5/2022 | Renock |
| 2022/0378680 A1 | 12/2022 | Ballhaus et al. |
| 2022/0378684 A1 | 12/2022 | Cochran et al. |
| 2022/0395444 A1 | 12/2022 | Hutton, III |
| 2023/0053056 A1 | 2/2023 | Renock et al. |

FOREIGN PATENT DOCUMENTS

| | | |
|---|---|---|
| CA | 1248458 A | 1/1989 |
| CA | 2078375 A1 | 3/1994 |
| CN | 1263455 A | 8/2000 |
| CN | 1286612 A | 3/2001 |
| CN | 1545404 A | 11/2004 |
| CN | 1823929 A | 8/2006 |
| CN | 100534415 C | 9/2009 |
| CN | 101112349 B | 5/2011 |
| CN | 101690697 B | 10/2011 |
| CN | 101559034 B | 1/2013 |
| CN | 102895151 A | 1/2013 |
| CN | 102973437 A | 3/2013 |
| CN | 102697668 B | 8/2013 |
| CN | 103356408 A | 10/2013 |
| CN | 102697670 B | 7/2014 |
| CN | 104107401 A | 10/2014 |
| CN | 102851015 B | 12/2014 |

(56) References Cited

FOREIGN PATENT DOCUMENTS

| | | | |
|---|---|---|---|
| CN | 105726393 A | 7/2016 |
| CN | 105769617 A | 7/2016 |
| CN | 106659664 A | 5/2017 |
| CN | 106750361 A | 5/2017 |
| CN | 107595657 A | 1/2018 |
| CN | 107595673 A | 1/2018 |
| CN | 107648096 A | 2/2018 |
| CN | 107737329 A | 2/2018 |
| CN | 108186385 A | 6/2018 |
| CN | 108283583 A | 7/2018 |
| CN | 110279591 A | 9/2019 |
| DE | 2145204 A1 | 3/1973 |
| DE | 3018456 A1 | 11/1981 |
| DE | 4315396 A1 | 11/1994 |
| DE | 102004012009 A1 | 9/2005 |
| DE | 202005009618 U1 | 9/2005 |
| DE | 102004023720 A1 | 12/2005 |
| DE | 102014225083 A1 | 10/2015 |
| DE | 102014225606 A1 | 10/2015 |
| DE | 102015204987 A1 | 9/2016 |
| EP | 0108517 A2 | 5/1984 |
| EP | 0574086 A2 | 12/1993 |
| EP | 0666358 A1 | 8/1995 |
| EP | 0674898 A2 | 10/1995 |
| EP | 1340485 A2 | 2/2003 |
| EP | 1346720 A2 | 9/2003 |
| EP | 067898 B2 | 3/2006 |
| EP | 1714678 A1 | 10/2006 |
| EP | 1842572 A2 | 10/2007 |
| EP | 2005939 A1 | 12/2008 |
| EP | 1970045 A3 | 9/2009 |
| EP | 2042216 B1 | 9/2015 |
| EP | 3260171 A1 | 12/2017 |
| EP | 3622946 A1 | 3/2020 |
| ES | 2052450 B1 | 12/1994 |
| FR | 2669531 A1 | 5/1992 |
| FR | 2795955 A1 | 1/2001 |
| GB | 190110699 A | 8/1901 |
| GB | 191023922 A | 10/1911 |
| GB | 1347950 A | 2/1974 |
| GB | 2048229 | 12/1980 |
| GB | 2450727 A | 1/2009 |
| JP | S56011009 A | 12/1981 |
| JP | S58113300 A | 7/1983 |
| JP | S58198412 A | 11/1983 |
| JP | AS60004598 A | 1/1985 |
| JP | S61236708 A | 10/1986 |
| JP | S62205200 A | 9/1987 |
| JP | S63165308 A | 7/1988 |
| JP | H04364114 A | 12/1992 |
| JP | H06220495 A | 8/1994 |
| JP | 07252134 A | 10/1995 |
| JP | H08310924 A | 11/1996 |
| JP | 09020618 A | 1/1997 |
| JP | 09030938 A | 2/1997 |
| JP | H09175961 A | 7/1997 |
| JP | H10017894 A | 1/1998 |
| JP | 2964226 B2 | 10/1999 |
| JP | 2000178586 A | 6/2000 |
| JP | 3069802 B2 | 7/2000 |
| JP | 2001011492 A | 1/2001 |
| JP | 2001011497 A | 1/2001 |
| JP | 2001254099 A | 9/2001 |
| JP | 2001261529 A | 9/2001 |
| JP | 2003201217 A | 12/2001 |
| JP | 2002179552 A | 6/2002 |
| JP | 2002226889 A | 8/2002 |
| JP | 2002336337 A | 11/2002 |
| JP | 2003055699 A | 2/2003 |
| JP | 2003082398 A | 3/2003 |
| JP | 2003171688 A | 6/2003 |
| JP | 2003176497 A | 6/2003 |
| JP | 2003261413 A | 9/2003 |
| JP | 2003268398 A | 9/2003 |
| JP | 3480165 B2 | 12/2003 |
| JP | 2003342131 A | 12/2003 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 2005232113 A | 9/2005 |
| JP | 2006063044 A | 3/2006 |
| JP | 2006104149 A | 4/2006 |
| JP | 2006124312 A | 5/2006 |
| JP | 2006183039 A | 7/2006 |
| JP | 2006193549 A | 7/2006 |
| JP | 2006249092 A | 9/2006 |
| JP | 2006282565 A | 10/2006 |
| JP | 2007131687 A | 5/2007 |
| JP | 2007177047 A | 7/2007 |
| JP | 2007223935 A | 9/2007 |
| JP | 2008001626 A | 1/2008 |
| JP | 2008214292 A | 9/2008 |
| JP | 2009096778 A | 5/2009 |
| JP | 2009120559 A | 6/2009 |
| JP | 2009161866 A | 7/2009 |
| JP | 2011153167 A | 8/2011 |
| JP | 2011190221 A | 9/2011 |
| JP | 2011241353 A | 12/2011 |
| JP | 5041113 B2 | 7/2012 |
| JP | 2013010757 A | 1/2013 |
| JP | 2013091641 A | 5/2013 |
| JP | 2013151434 A | 8/2013 |
| JP | 2013155143 A | 8/2013 |
| JP | 2013216639 A | 10/2013 |
| JP | 6046394 B2 | 1/2014 |
| JP | 2014024875 A | 2/2014 |
| JP | 2014091723 A | 5/2014 |
| JP | 5667790 B2 | 2/2015 |
| JP | 2015101545 A | 6/2015 |
| JP | 2016013973 A | 1/2016 |
| JP | 6184550 B1 | 8/2017 |
| JP | 2018012673 A | 1/2018 |
| KR | 100290589 B1 | 9/2001 |
| KR | 100821846 81 | 4/2008 |
| KR | 1020080111280 A | 12/2008 |
| KR | 20090095359 A | 9/2009 |
| KR | 20100040180 A | 4/2010 |
| KR | 20140060882 A | 5/2014 |
| KR | 101494008 B1 | 2/2015 |
| KR | 101503922 81 | 3/2015 |
| KR | 101532070 B1 | 7/2015 |
| UA | 50333 U | 5/2010 |
| WO | 8603679 A1 | 7/1986 |
| WO | 9114759 A1 | 10/1991 |
| WO | 91017237 A1 | 11/1991 |
| WO | 9213520 A1 | 8/1992 |
| WO | 199325650 A1 | 12/1993 |
| WO | 9417783 A2 | 8/1994 |
| WO | 9502389 A2 | 1/1995 |
| WO | 9726854 A1 | 7/1997 |
| WO | 9823258 A1 | 6/1998 |
| WO | 9906010 A2 | 2/1999 |
| WO | 9918928 A1 | 4/1999 |
| WO | 9924004 A1 | 5/1999 |
| WO | 9924013 A1 | 5/1999 |
| WO | 9949837 A1 | 10/1999 |
| WO | 9957233 A1 | 11/1999 |
| WO | 0012553 A1 | 3/2000 |
| WO | 0032601 | 6/2000 |
| WO | 0119949 A1 | 3/2001 |
| WO | 0142409 A1 | 6/2001 |
| WO | 0148021 A1 | 7/2001 |
| WO | 2001076552 A2 | 10/2001 |
| WO | 2003051319 A1 | 6/2003 |
| WO | 03096998 A1 | 11/2003 |
| WO | 2004078901 A1 | 9/2004 |
| WO | 2005023975 A1 | 3/2005 |
| WO | 2008017540 A1 | 2/2008 |
| WO | 2008128826 A1 | 10/2008 |
| WO | 2008145582 A1 | 12/2008 |
| WO | 2009016555 A2 | 2/2009 |
| WO | 2009030594 A1 | 3/2009 |
| WO | 2009053931 A2 | 4/2009 |

(56) References Cited

FOREIGN PATENT DOCUMENTS

| | | |
|---|---|---|
| WO | 2010026009 A1 | 3/2010 |
| WO | 2010052147 A2 | 5/2010 |
| WO | 2012017091 A2 | 2/2012 |
| WO | 2012052536 A2 | 4/2012 |
| WO | 2012055587 A1 | 5/2012 |
| WO | 2012055812 A1 | 5/2012 |
| WO | 2012084970 A1 | 6/2012 |
| WO | 2012127009 A1 | 9/2012 |
| WO | 2012136651 A1 | 10/2012 |
| WO | WO-2012162331 A2 * 11/2012 ............... A61K 8/31 |
| WO | 2013010706 A2 | 1/2013 |
| WO | 2013018805 A1 | 2/2013 |
| WO | 2013119908 A1 | 8/2013 |
| WO | 2014073245 A1 | 5/2014 |
| WO | 2014073456 A1 | 5/2014 |
| WO | 2014111667 A2 | 7/2014 |
| WO | 2014111668 A2 | 7/2014 |
| WO | 2014148245 A1 | 9/2014 |
| WO | 2015067779 A1 | 5/2015 |
| WO | 2015085376 A1 | 6/2015 |
| WO | 2015122371 A1 | 8/2015 |
| WO | 2015141787 A1 | 9/2015 |
| WO | 2016049389 A1 | 3/2016 |
| WO | 2016147196 A1 | 9/2016 |
| WO | 2017052161 A1 | 3/2017 |
| WO | 2017140798 A1 | 8/2017 |
| WO | 2017140802 A1 | 8/2017 |
| WO | 2017207685 A1 | 12/2017 |
| WO | 2018023180 A1 | 2/2018 |
| WO | 2018109148 A1 | 6/2018 |
| WO | 2019030458 A2 | 2/2019 |
| WO | 2019074990 A1 | 4/2019 |
| WO | 2019074992 A1 | 4/2019 |
| WO | 2019200027 A1 | 10/2019 |
| WO | 2020005309 A1 | 1/2020 |
| WO | 2020030732 A1 | 2/2020 |
| WO | 2021026572 A1 | 2/2021 |
| WO | 2021099088 A1 | 5/2021 |
| WO | 2021127318 A1 | 6/2021 |
| WO | 2021231510 A1 | 11/2021 |

OTHER PUBLICATIONS

ASTM D3954-94, Reapproved 2010, vol. 15.04, Standard Test Method for Dropping Point of Waxes.
Brattoli et al. Odour Detection Methods: Olfactometry and Chemical Sensors. Sensors (Basel), 2011; 11(5); 5290-5322 (2011).
Chemical Book (Chemical Book, Isolongifolone, available at http://www.chemicalbook.com/ProductChemicalPropertiesCB5318980_EN.htm).
Crepaldi, E.L., et al., Chemical, Structural, and Thermal Properties of Zn(II)-Cr(III) Layered Double Hydroxides Intercalated with Sulfated and Sulfonated Surfactants, Journal of Colloid and Interface Science, 2002, pp. 429-442, vol. 248.
Database GNPD [Online] MINTEL;Mar. 28, 2018 (Mar. 28, 2018),anonymous: Dandruff Control Shampoo 11, XP055787038,Database accession No. 5556267abstract.
Database GNPD [Online] MINTEL;Apr. 5, 2005 (Apr. 5, 2005),anonymous: "Anticaspa-Graso Anti-DandruffShampoo", XPC:155787029,Database accession No. 351776paragraph [ingredients].
Database WPI; Week 201459; Thomson scientific, London, GB; AN 2014-P66521; XP002752638.
Grillet et al., "Polymer Gel Rheology and Adhesion", Rheology, 2012, pp. 59-80.
McGinley et al. American Association of Textile Chemists and Colorists, 2017, 17 pages, (2017).
McGinley et al. Performance Verification of Air Freshener Products and Other Odour Control Devices for Indoor Air Quality Malodours. Presented at the 8th Workshop on Odour and Emissions of Plastic Materials Universitat Kassel Institut for Wesrkstofftechnik Kassel, Germany, Mar. 27-28, 2006, 13 pages.

Morioka, H. et al. "Effects of Zinc on the New Preparation Method of Hydroxy Double Salts" Inorg. Chem. 1999, 38, 4211-6.
Sensory.,"A Review of the Science and Technology of Odor Measurement", Prepared for the Air Quality Bureau of the Iowa Department of Natural Resources, Dec. 30, 2005 51 pages.
Todd et al., Volatile Silicone Fluids for Cosmetics, Cosmetics and Toiletries, vol. 91, pp. 27-32 (Jan. 1976).
PCT Search Report and Written Opinion for PCT/US2021/061703 dated May 25, 2022, 26 pages.
BASF, "Practical Guide to Rheology Modifiers", download from https://insights.basf.com/files/BASF_ED_RheologyModifiers_download.pdf on Nov. 1, 2022. (Year: 2022).
"Personal care solutions Guide", Solvay, Publication date: May 2018, 84 pages.
Product Data Record Tego®Betain F KB 5, dated Jul. 1, 2015, 4 pages.
Anonymous: "Anti-Dandruff Scalp Care Shampoo", MINTEL, Database accession No. 301924, Sep. 16, 2004, 2 pages.
"Anti-Dandruff Shampoo", Mintel Database, Record No. 752198, dated Aug. 2007 ; pp. 1-3.
"Dandruff Control Shampoo", Mintel Database, Record No. 2300131, dated Jan. 2014; pp. 1-2.
"Foam & chemical contamination in waterways", Retrieved From https://www.epa.nsw.gov.au/-/media/epa/corporate-site/resources/epa/foam-chemical-contamination-in-waterway.pdf, Dec. 2015, 2 Pages.
"Natural Detangling Shampoo", Mintel Database, dated Sep. 13, 2017; 2 pages.
"Soda Shampoo", Mintel Database, dated Apr. 2015; pp. 1-4.
"Treatment Foam for Recurrent Scaling Conditions", Mintel Database, Aug. 2007; pp. 1-2.
Acne Foaming Cleanser, Database accession No. 4172863, Jul. 29, 2016, 3 pages.
Anonymous: "MERQUAT Polyquaternium 47 Series, Water Soluble Polymers for Personal Care", Jul. 30, 2017, URL: https://www.in-cosmetics.com/_novadocuments/2729, retrieved on Dec. 21, 2018 ; 1 page.
Anonymous: "Naturally Derived Body Wash", Database GNPD [Online] MINTEL; Feb. 15, 2021, 2 pages.
Anonymous: "Peptide Shampoo", Database GNPD [Online] MINTEL; Dec. 14, 2015, 3 pages.
Anonymous: "Replenishing Moisture Shampoo", Database GNPD [Online] MINTEL, Mar. 10, 2015br.
Anonymous: "Shampoo", Database GNPD [Online] MINTEL, Jan. 26, 2021, 3 pages.
Anonymous: "Shampooing au Phytolait d'abricot—Formule N°102-MP06-MI3-AA03",Internet Citation, Feb. 19, 2005, Retrieved from the Internet:URL: http://web.archive.org/web/20050219040350/www.albanmuller.com/francais/catalogue/formules/formul10.asp, 1 page.
Carbopol Aqua SF-1 Polymer Technical Data Sheet, TDS-294, dated Dec. 2000 ; pp. 1-9.
Christensen et al., "Experimental Determination of Bubble Size Distribution in a Water Column by Interferometric Particle Imaging and Telecentric Direct Image Method", Student Report, Aalborg University; dated Jun. 3, 2014; 123 pages.
D'Souza et al., Shampoo and Conditioners: What a Dermatologist Should Know? Indian J Dermatol, dated May-Jun. 2015; pp. 60(3), 248-254 (2015).
Database GNPD [Online] MINTEL; Jan. 6, 2020 (Jan. 6, 2020),anonymous: 11 Shampoo 11, 3 pages.
Datasheet: Empigen Total Active TC/U, Datasheet, dated Jan. 31, 2017 (Innospec) ; 2 pages.
Dehyquart Guar: Published dated Nov. 2010 ; pp. 1-34.
Fevola, Michael J. "Guar Hydroxypropyltrimonium Chloride." Cosmetics and toiletries; vol. 127.1; Jan. 2012 ; pp. 16-21.
Hair Care/Conditioning Polymers Differentiation, Anonymous, Feb. 1, 2017, URL: http://www.biochim.it/assets/site/media/allegati/cosmetica/hair-care/tab-merquat-hair-care.pdf, retrieved on Dec. 20, 2018; p. 1.
Happi: "Sulfate-Free Surfactants Conditioning Shampoo", Retrieved from the Internet:URL:https://www.happi.com/contents/view_

(56) References Cited

OTHER PUBLICATIONS formulary/2009-10-01/sulfate-free-surfactants-conditioning-shampoo/, XP002804301, Jan. 10, 2019, 1 page.
Inspection certificate for Hostapon® CCG, Clariant Ibérica Production, S.A., May 6, 2019; p. 1-2.
Medvedev, Diffusion Coefficients in Multicomponent Mixtures, PhD Thesis from Technical University of Denmark, dated 2005, 181 pages.
Mintel GNPD Base, Bright Blonde Shampoo Record No. 3412889 Feb. 29, 2016 ; 2 pages.
Mintel GNPD Base, Mineral Conquer Blonde Silver Shampoo Record No. 3953107 Apr. 30, 2016; 2 pages.
Mintel GNPD Base, Royal Treatment Collection, Record No. 1946223 dated Dec. 31, 2011, 3 pages.
Musazzi, "Emulsion versus nonoemulsion: how much is the formulative shift critical for a cosmetic product?" (Drug Deliv. and Trans. Res. (2018) 8: pp. 414-421 (Year: 2018).
Natural oils: why specific carbon chains are chosen for certain surfactant properties, Chemlink, URL Link: https://www.chemlink.co.uk/natural-oils-why-specific-carbon-chains-are-chosen-for-certain-surfactant-properties/a (Year: 2022), 4 pgs.
Naturally Rich Moisturizing Shampoo, Database accession No. 6421011, Mar. 27, 2019, 3 pages.
Noritomi H. Formation and Solubilization Property of Water-in-Oil Microemulsions of Alkyl Glucoisdes. Advances in Nanoparticles, 2013, 2, 366-371 (Year: 2013).
Parchem fine & specialty chemicals. MIPA-laureth sulfate supplier distributor—CAS 83016-76-6; dated 2021; pp. 1-7.
PERM Inc, , Diffusion Coefficient: Measurement Techiques, https://perminc.com/resources/fundamentals-of-fluid-flow-in-porous-media/chapter-3-molecular-diffusion/diffusion-coefficient/measurement-techniques, dated Oct. 2020; p. 1-4.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-the Safety-Assessment-of-Polyquaternium-10.pdf, retrieved on Dec. 20, 2018; 9 pages.
Practical Modern Hair Science, Published 2012; 43 pages.
Product Bulletin, Amphosol® CG, Cocamidopropyl Betaine, Stepan Company, Jun. 2011; 1-2 pages.
Product Data Sheet for Chemoryl™ LS Surfactant, Sodium Lauroyl Sarcosinate, Lubrizol Advanced Materials, Inc., Mar. 24, 2020; 1-2 pages.
Product Data Sheet, Eversoft™ UCS-40S, Disodium Cocoyl Glutamate (Sodium Cocoyl Glutamate*), Sino Lion USA, Jul. 2018; 2 pages.
Product Fact Sheet—Hostapon® CCG, mild anionic surfactant for the cosmetic industry, Clariant International Ltd., Aug. 2014 ; 1-3 pages.
Product Fact Sheet, Hostapon® CGN, Mild anionic surfactant for the cosmetic industry, Clariant International Ltd., Jan. 2016; 1-2 pages.
Rajendran A. et al: "Study on the Analysis of Trace Elements in Aloe veraand Its Biological Importance Study on the Analysis of Trace Elements in Aloe vera and Its Biological Importance", Journal of Applied Sciences Research, Jan. 1, 2007 (Jan. 1, 2007), XP055799133, pp. 1476-1478.
Robinson et al., Final Report of the Amended Safety Assessment of Sodium Laureth Sulfate and Related Salts of SulfatedEthoxylated Alcohols, International Journal of Toxicology 29 (Supplement 3); dated 2010; pp. 151S-161S.
S. Herrwerth et al.: "Highly Concentrated Cocamidopropyl Betaine— The Latest Developments for Improved Sustainability and Enhanced Skin Care", Tenside, Surfactants, Detergents, vol. 45, No. 6, dated Nov. 1, 2008, pp. 304-308, p. 305—left-hand column; 3 pages.
Safety assessment of amino acid alkyl amides used in cosmetics , dated Sep. 20, 2013, 46 pages.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012; 1-2 pages.
Shampoo C, Database accession No. 1632217, Sep. 29, 2011, 3 pages.
Softazoline CL-R, Kawaken Singapore PTE Ltd. Website printout from http://kawaken.com.sg/softazoline-ch-r//a, accessed on Nov. 30, 2022.
UL Prospector® Product Data Sheet, Plantacare® 818 UP, C8-16 fatty alcohol glucoside, BASF, dated May 21, 2015; 1-3 pages.
Unhale Shrikrushna Subhash et al: Formulation and Development of Sulphate Free Shampoo About an Updates andGuidelines of Corona Virus View project health and beauty science View project Rohit Bhavsar Reliance Industries Limited; International Journal for Research inApplied Science & Engineering Technology, Apr. 1, 2020 (Apr. 1, 2020)t XP055842327, DOI: 10.22214, 14 pages.
"Deep Image Matting", Ning Xu et al, Beckman Institute for Advanced Science and Technology, University of Illinois at Urbana-Champaign, Adobe Research, dated Mar. 10, 2017; 10 pages.

* cited by examiner

HAIR CARE COMPOSITIONS COMPRISING MALODOR REDUCTION MATERIALS

FIELD OF THE INVENTION

The present invention relates to hair care compositions comprising malodor reduction compositions and methods of making and using such hair care compositions.

BACKGROUND OF THE INVENTION

Unscented or lightly scented products are desired by consumers as they may be considered more natural and discreet than more highly scented products. Manufacturers of unscented or lightly scented products for controlling malodors rely on malodor reduction ingredients or other technologies (e.g. filters) to reduce malodors. However, effectively controlling malodors, for example, amine-based malodors (e.g. fish and urine), thiol and sulfide-based malodors (e.g. garlic and onion), $C_2$-$C_{12}$ carboxylic acid based malodors (e.g. body and pet odor), indole based malodors (e.g. fecal and bad breath), short chain fatty aldehyde based malodors (e.g. grease) and geosmin based malodors (e.g. mold/mildew) may be difficult, and the time required for a product to noticeably reduce malodors may create consumer doubt as to the product's efficacy on malodors. Often times, manufacturers incorporate scented perfumes to help mask these difficult malodors.

Unfortunately, malodor control technologies typically cover up the malodor with a stronger scent and thus interfere with the scent of the perfumed or unperfumed situs that is treated with the malodor control technology. Thus, limited nature of the current malodor control technologies is extremely constraining. Thus what is needed is a broader palette of malodor control technologies so the perfume community can deliver the desired level of character in a greater number of situations/applications. Surprisingly, Applicants recognized that in addition to blocking a malodor's access to a receptor cell, in order to achieve the desired goal, a malodor control technology must leave such receptor cell open to other molecules, for example scent molecules. Thus, hair care compositions comprising the malodor control technologies disclosed herein provide malodor control without leaving an undesirable scent and, when perfume is used to scent such compositions, such scent is not unduly altered by the malodor control technology.

Sulfur containing anti-fungal hair and scalp care compositions provide some of the most effective protection from and relief of dandruff conditions. Historically, sulfur and other sulfur-based formulations are highly medicinal and pungent smelling—both in use and throughout the day—due to residual sulfur compounds deposited on the hair and scalp and its interactions with hair and skin. These significant negative cosmetic attributes may cause consumers to avoid sulfur and other sulfur-based formulations and therefore product usage compliance is difficult and as a result consumers often do not find complete relief from their dandruff condition.

SUMMARY OF THE INVENTION

The present invention is directed to a hair care composition comprising, based on total composition weight, a) a sum total of from about 0.1% to about 2% of a perfume with one or more malodor reduction materials having a wt % from about 0.0001% to about 2% of one or more of said malodor reduction materials; b) from about 0.01% to about 10% of a scalp active material selected from the group consisting of sulfur and mixtures thereof; c) from about 0.1% to about 40% of a surfactant.

DETAILED DESCRIPTION OF THE INVENTION

Definitions

"Hair Care Composition" as Defined Herein, May Include Shampoos, Conditioners and Leave-On-Treatments "Rinse-off" means the intended product usage includes application to hair followed by rinsing and/or wiping the product from the skin and/or hair within a few seconds to minutes of the application step.

"STnS" refers to sodium trideceth(n) sulfate, wherein n can define the average number of moles of ethoxylate per molecule.

As used herein "MORV" is the calculated malodor reduction value for a subject material. A material's MORV indicates such material's ability to decrease or even eliminate the perception of one or more malodors. For purposes of the present application, a material's MORV is calculated in accordance with method found in the test methods section of the present application.

As used herein, "malodor" refers to compounds generally offensive or unpleasant to most people, such as the complex odors associated with bowel movements.

As used herein, "odor blocking" refers to the ability of a compound to reduce the perception of a malodor.

As used herein, the term "perfume" does not include malodor reduction materials. Thus, the perfume portion of a composition does not include, when determining the perfume's composition, any malodor reduction materials found in the composition as such malodor reduction materials are described herein. In short, if a material has a malodor reduction value "MORV" that is within the range of the MORV recited in the subject claim, such material is a malodor reduction material for purposes of such claim.

As used herein, PRM is the abbreviation form for perfume raw material.

As used herein, the terms "a" and "an" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Hair Care Compositions

Rinse-off hair care compositions can come in a variety of forms. For example, a hair care composition can be in a liquid form and can be a shampoo, conditioning shampoo, Hair Care compositions can include perfume materials. Many consumers prefer hair care compositions that can consistently provide a desired scent, or odor that can be perceived each time the product is used. Perfume materials can provide the desired scent or odor to these hair care compositions. These perfume (i.e., fragrance) materials can include perfumes, perfume raw materials, and perfume delivery systems. The present invention may have a sum total of from about 0.1% to about 2% of a perfume with one or more malodor reduction materials; may have a sum total of from about 0.5% to about 1.5% of a perfume with one or more malodor reduction materials; may have a sum total of from about 0.8% to about 1.2% of a perfume with one or more malodor reduction materials; may have a sum total of from about 0.85% to about 1.0% of a perfume with one or more malodor reduction materials.

Malodor Reduction Materials

A non-limiting set of suitable malodor reduction materials are provided in the tables below. In the present invention, the malodor reduction material may be selected from one or more perfume raw materials.

TABLE 1

List of materials with Sulfur MORV > 3

| Number | CAS Number | Name | VP@ 25 C. (Torr) | ClogP | MORV |
|---|---|---|---|---|---|
| 1 | 188199-50-0 | 2'-isopropyl-1,7,7-trimethylspiro[bicyclo[2.2.1]heptane-2,4'4-[1,3]dioxane] | 2.3E−02 | 4.30 | 3.04 |
| 2 | 154171-77-4 | (1',1',5',5'-tetramethylhexahydro-2'H,5'H-spiro[[1,3]dioxolane-2,8'-[2,4a]methanonaphthalene] | 1.5E−02 | 4.51 | 4.66 |
| 3 | 5413-60-5 | 3a,4,5,6,7,7a-hexahydro-1H-4,7-methanoinden-6-yl acetate) | 1.4E−02 | 2.79 | 3.44 |
| 4 | 68480-11-5 | Decahydro-3H-spiro[furan-2,5'-[4,7]methanoindene] | 1.4E−02 | 3.36 | 3.22 |
| 5 | 19870-74-7 | CEDRYL METHYL ETHER | 1.3E−02 | 5.08 | 5.52 |
| 6 | 116126-82-0 | Ethyl (1R, 2R, 3R, 4R)-3-isopropylbicyclo[2.2.1]hept-5-ene-2-carboxylate | 1.2E−02 | 3.68 | 3.22 |
| 7 | 3738-00-9 | 3aR,5aR,9aR,9bR)-3a,6,6,9a-tetramethyldodecahydronaphtho[2,1-b]furan | 9.3E−03 | 5.11 | 3.06 |
| 8 | 33885-52-8 | alpha,alpha,6,6-tetramethyl bicyclo[3.1.1]hept-2-ene-propanal | 6.9E−03 | 4.31 | 3.18 |
| 9 | 1139-30-6 | 4,5-epoxy-4,11,11-trimethyl-8-methylenebicyclo(7.2.0)undecane | 6.7E−03 | 4.47 | 3.57 |
| 10 | 41724-19-0 | 4aR,8aS)-7-methyloctahydro-1,4-methanonaphthalen-6(2H)-one | 6.5E−03 | 2.66 | 3.43 |
| 11 | 86803-90-9 | 5-methoxyoctahydro-1H-4,7-methanoindene-2-carbaldehyde | 4.4E−03 | 2.08 | 3.87 |
| 12 | 68738-96-5 | 8,8-dimethyl-6,7-dihydro-5H-naphthalene-2-carbaldehyde | 4.4E−03 | 3.92 | 3.11 |
| 13 | 41816-03-9 | 2R,4a'R,8a'R)-3,7'-dimethyl-3',4',4a',5',8',8a'-hexahydro-1'H-spiro[oxirane-2,2'-[1,4]methanonaphthalene]) | 3.3E−03 | 3.09 | 3.57 |
| 14 | 476332-65-7 | (2,2,6,6,7,8,8-heptamethyldecahydro-2H-indeno[4,5-b]furan | 3.2E−03 | 6.14 | 5.66 |
| 15 | 23787-90-8 | 1,3,4,6,7,8alpha-hexahydro-1,1,5,5-tetramethyl-2H-2,4alpha-methanophtalen-8(5H)-one) | 2.6E−03 | 4.09 | 4.53 |
| 16 | 67634-20-2 | 3a,4,5,6,7,7a-hexahydro-1H-4,7-methanoinden-5-yl isobutyrate | 2.4E−03 | 3.51 | 4.13 |
| 17 | 57345-19-4 | 3S,5aR,7aS,11aS,11bR)-3,8,8,11a-tetramethyldodecahydro-5H-3,5a-epoxynaphtho[2,1-c]oxepine | 2.0E−03 | 5.18 | 4.97 |
| 18 | 68912-13-0 | (8,8-dimethyl-3a,4,5,6,7,7a-hexahydro-1H-4,7-methanoinden-6-yl propionate) | 1.8E−03 | 4.00 | 5.04 |
| 19 | 211299-54-6 | 4aR,5R,7aS,9R)-2,2,5,8,8,9a-hexamethyloctahydro-4H-4a,9-methanoazuleno[5,6-d][1,3]dioxole | 1.8E−03 | 4.85 | 6.82 |
| 20 | 68901-32-6 | 2-(8-isopropyl-6-methylbicyclo[2.2.2]oct-5-en-2-yl)-1,3-dioxolane | 1.2E−03 | 3.81 | 3.04 |
| 21 | 68039-44-1 | 3a,4,5,6,7,7a-hexahydro-1H-4,7-methanoinden-6-yl pivalate | 1.2E−03 | 3.96 | 3.79 |
| 22 | 823178-41-2 | 3a,5,6,7,8,8b-hexahydro-2,2,6,6,7,8,8-heptamethyl-4H-indeno(4,5-d)-1,3-dioxole | 7.4E−04 | 4.97 | 5.24 |

TABLE 1-continued

List of materials with Sulfur MORV > 3

| Number | CAS Number | Name | VP@ 25 C. (Torr) | ClogP | MORV |
|---|---|---|---|---|---|
| 23 | 39900-38-4 | (3R-(3alpha,3a,6alpha,7,8aalpha))-octahydro-3,6,8,8-tetramethyl-1H-3a,7-methanoazulen-6-yl formate | 6.3E−04 | 4.97 | 4.83 |
| 24 | 77-53-2 | (1S,2R,5S,7R,8R)-2,6,6,8-tetramethyltricyclo[5.3.1.01,5]undecan-8-ol | 5.7E−04 | 4.49 | 4.40 |
| 25 | 54464-57-2 | 1-((2S,3S)-2,3,8,8-tetramethyl-1,2,3,4,5,6,7,8-octahydronaphthalen-2-yl)ethan-1-one | 5.4E−04 | 4.72 | 3.26 |
| 26 | 30168-23-1 | ((E)-4-((3aS,7aS)-octahydro-5H-4,7-methanoinden-5-ylidene)butanal | 4.4E−04 | 3.97 | 4.42 |
| 27 | 5986-55-0 | 1R-(1alpha,4beta,4aalpha,6beta,8aalpha))-octahydro-4,8a,9,9-tetramethyl-1,6-methanol (2H)-naphthol | 2.8E−04 | 4.46 | 4.34 |
| 28 | 32214-91-8 | [(3Z)-4,11,11-trimethyl-8-methylidene-5-bicyclo[7.2.0]undec-3-enyl] acetate | 2.5E−04 | 5.50 | 3.55 |
| 29 | 552-02-3 | (1aR,4S,4aS,7R,7aS,7bS)-1,1,4,7-tetramethyldecahydro-1H-cyclopropa[e]azulen-4-ol | 1.8E−04 | 4.72 | 4.12 |
| 30 | 69486-14-2 | Z)-6-ethylideneoctahydro-2H-5,8-methanochromen-2-one) | 1.1E−04 | 2.32 | 3.82 |
| 31 | 32388-55-9 | 1-((3R,3aR,7R,8aS)-3,6,8,8-tetramethyl-2,3,4,7,8,8a-hexahydro-1H-3a,7-methanoazulen-5-yl)ethan-1-one | 8.5E−05 | 4.97 | 4.49 |
| 32 | 167254-80-0 | 3,5,5,6,7,8,8-heptamethy1-5,6,7,8-tetrahydronaphthalene-2-carbonitrile | 6.9E−05 | 5.88 | 3.36 |
| 33 | 66072-32-0 | 4-(1,7,7-trimethyl-6-bicyclo[2.2.1]heptanyl)cyclohexan-1-ol | 3.0E−05 | 4.45 | 3.50 |
| 34 | 501929-47-1 | (E)-4-((3aR,4R,7R,7aR)-1,3a,4,6,7,7a-hexahydro-5H-4,7-methanoinden-5-ylidene)-3-methylbutan-2-ol | 8.5E−06 | 3.87 | 5.44 |
| 35 | 3681-73-0 | (E)-3,7-dimethylocta-2,6-dien-1-yl palmitate) | 3.0E−09 | 10.75 | 3.31 |
| 36 | 1222-05-5 | 1,3,4,6,7,8-hexahydro-4,6,6,7,8,8,-hexamethyl-cyclopenta[g]benzopyran | 4.14E−04 | 5.93 | 4.46 |
| 37 | 1392325-86-8 | 5H-Cyclopenta[h]quinazoline, 6,6a,7,8,9,9a-hexahydro-7,7,8,9,9-pentamethyl- | 2.92E−04 | 5.02 | 3.98 |
| 38 | 24851-98-7 | Cyclopentaneacetic acid, 3-oxo-2-pentyl-, methyl ester | 7.10E−04 | 2.87 | 3.44 |
| 39 | 3407-42-9 | Cyclohexanol, 3-(5,5,6-trimethylbicyclo[2.2.1]hept-2-yl)- | 1.90E−05 | 4.40 | 3.95 |
| 40 | 37172-53-5 | Cyclopentanecarboxylic acid, 2-hexyl-3-oxo-, methyl ester | 6.75E−04 | 2.89 | 3.47 |
| 41 | 6790-58-5 | Naphtho[2,1-b]furan, dodecahydro-3a,6,6,9a-tetramethyl-, (3aR,5aS,9aS,9bR)- | 9.34E−03 | 5.11 | 3.06 |
| 42 | 68155-66-8 | Ethanone, 1-(1,2,3,5,6,7,8,8a-octahydro-2,3,8,8-tetramethyl-2-naphthalenyl)- | 5.65E−04 | 4.75 | 3.27 |
| 43 | 68155-67-9 | Ethanone, 1-(1,2,3,4,6,7,8,8a-octahydro-2,3,8,8-tetramethyl-2-naphthalenyl)- | 5.65E−04 | 5.19 | 3.23 |
| 44 | 68991-97-9 | 2-Naphthalenecarboxaldehyde, 1,2,3,4,5,6,7,8-octahydro-8,8-dimethyl- | 4.36E−03 | 3.92 | 3.11 |
| 45 | 77-54-3 | 1H-3a,7-Methanoazulen-6-ol, octahydro-3,6,8,8-tetramethyl-, 6-acetate, (3R,3aS,6R,7R,8aS)- | 1.92E−03 | 5.31 | 4.69 |
| 46 | 472-97-9 | Tricyclo[6.3.1.02,5]dodecan-1-ol, 4,4,8-trimethyl-, (1R,2S,5R,8S)- | 1.63E−04 | 4.52 | 4.00 |
| 47 | 16223-63-5 | 1H-3a,6-Methanoazulene-3-methanol, octahydro-7,7-dimethyl-8-methylene-, (3S,3aR,6R,8aS)- | 4.40E−05 | 3.52 | 4.29 |
| 48 | 67801-36-9 | 1H-Indole-1-heptanol, η-1H-indol-1-yl-α,α,ε-trimethyl- | 8.72E−14 | 6.27 | 4.63 |

TABLE 2

| | | | VP@ | | |
|---|---|---|---|---|---|
| | CAS | | 25 C. | | |
| Number | Number | Name | (Torr) | ClogP | MORV |

Sulfor MORV > 3 and ClogP > 3

| Number | CAS Number | Name | VP@ 25 C. (Torr) | ClogP | MORV |
|---|---|---|---|---|---|
| 1 | 188199-50-0 | 2'-isopropyl-1,7,7-trimethylspiro[bicyclo[2.2.1]heptane-2,4'-[1,3]dioxane | 2.3E−02 | 4.30 | 3.04 |
| 2 | 154171-77-4 | (1',1',5',5'-tetramethylhexahydro-2'H,5'H-spiro[[1,3]dioxolane-2,8'-[2,4a]methanonaphthalene] | 1.5E−02 | 4.51 | 4.66 |
| 4 | 68480-11-5 | Decahydro-3H-spiro[furan-2,5'-[4,7]methanoindene] | 1.4E−02 | 3.36 | 3.22 |
| 5 | 19870-74-7 | CEDRYL METHYL ETHER | 1.3E−02 | 5.08 | 5.52 |
| 6 | 116126-82-0 | Ethyl (1R,2R,3R,4R)-3-isopropylbicyclo[2.2.1]hept-5-ene-2-carboxylate | 1.2E−02 | 3.68 | 3.22 |
| 7 | 3738-00-9 | 3aR,5aR,9aR,9bR)-3a,6,6,9a-tetramethyldodecahydronaphtho[2,1-b]furan | 9.3E−03 | 5.11 | 3.06 |
| 8 | 33885-52-8 | alpha,alpha,6,6-tetramethyl bicyclo[3.1.1]hept-2-ene-propanal | 6.9E−03 | 4.31 | 3.18 |
| 9 | 1139-30-6 | 4,5-epoxy-4,11,11-trimethyl-8-methylenebicyclo(7.2.0)undecane) | 6.7E−03 | 4.47 | 3.57 |
| 12 | 68738-96-5 | 8,8-dimethyl-6,7-dihydro-5H-naphthalene-2-carbaldehyde | 4.4E−03 | 3.92 | 3.11 |
| 13 | 41816-03-9 | 2R,4a'R,8a'R)-3,7'-dimethyl-3',4',4a',5',8',8a'-hexahydro-1'H-spiro[oxirane-2,2'-[1,4]methanonaphthalene]) | 3.3E−03 | 3.09 | 3.57 |
| 14 | 476332-65-7 | (2,2,6,6,7,8,8-heptamethyldecahydro-2H-indeno[4,5-b]furan | 3.2E−03 | 6.14 | 5.66 |
| 15 | 23787-90-8 | 1,3,4,6,7,8alpha-hexahydro-1,1,5,5-tetramethyl-2H-2,4alpha-methanophtalen-8(5H)-one) | 2.6E−03 | 4.09 | 4.53 |
| 16 | 67634-20-2 | 3a,4,5,6,7,7a-hexahydro- 1H-4,7-methanoinden-5-yl isobutyrate | 2.4E−03 | 3.51 | 4.13 |
| 17 | 57345-19-4 | 3S,5aR,7aS,11aS,11bR)-3,8,8,11a-tetramethyldodecahydro-5H-3,5a-epoxynaphtho[2,1-c]oxepine | 2.0E−03 | 5.18 | 4.97 |
| 18 | 68912-13-0 | (8,8-dimethyl-3a,4,5,6,7,7a-hexahydro-1H-4,7-methanoinden-6-yl propionate) | 1.8E−03 | 4.00 | 5.04 |
| 19 | 211299-54-6 | 4aR,5R,7aS,9R)-2,2,5,8,8,9a-hexamethyloctahydro-4H-4a,9-methanoazuleno[5,6-d][1,3]dioxole | 1.8E−03 | 4.85 | 6.82 |
| 20 | 68901-32-6 | 2-(8-isopropyl-6-methylbicyclo[2.2.2]oct-5-en-2-yl)-1,3-dioxolane | 1.2E−03 | 3.81 | 3.04 |
| 21 | 68039-44-1 | 3a,4,5,6,7,7a-hexahydro-1H-4,7-methanoinden-6-yl pivalate | 1.2E−03 | 3.96 | 3.79 |
| 22 | 823178-41-2 | 3a,5,6,7,8,8b-hexahydro-2,2,6,6,7,8,8-heptamethyl-4H-indeno(4,5-d)-1,3-dioxole | 7.4E−04 | 4.97 | 5.24 |
| 23 | 39900-38-4 | (3R-(3alpha, 3a,6alpha,7,8aalpha))-octahydro-3,6,8,8-tetramethyl-1H-3a,7-methanoazulen-6-yl formate | 6.3E−04 | 4.97 | 4.83 |
| 24 | 77-53-2 | (1S,2R,5S,7R,8R)-2,6,6,8-tetramethyltricyclo[5.3.1.01,5]undecan-8-ol | 5.7E−04 | 4.49 | 4.40 |
| 25 | 54464-57-2 | 1-((2S,3S)-2,3,8,8-tetramethyl-1,2,3,4,5,6,7,8-octahydronaphthalen-2-yl)ethan-1-one | 5.4E−04 | 4.72 | 3.26 |
| 26 | 30168-23-1 | ((E)-4-((3aS ,7aS)-octahydro-5H-4,7-methanoinden-5-ylidene)butanal | 4.4E−04 | 3.97 | 4.42 |
| 27 | 5986-55-0 | 1R-(1alpha,4beta,4aalpha,6beta,8aalpha))-octahydro-4,8a,9,9-tetramethyl-1,6-methano-1(2H)-naphthol | 2.8E−04 | 4.46 | 4.34 |
| 28 | 32214-91-8 | [(3Z)-4,11,11-trimethyl-8-methylidene-5-bicyclo[7.2.0]undec-3-enyl] acetate | 2.5E−04 | 5.50 | 3.55 |
| 29 | 552-02-3 | (1aR,4S,4aS,7R,7aS,7bS)-1,1,4,7-tetramethyldecahydro-1H-cyclopropa[e]azulen-4-ol | 1.8E−04 | 4.72 | 4.12 |

TABLE 2-continued

Sulfor MORV > 3 and ClogP > 3

| Number | CAS Number | Name | VP@ 25 C. (Torr) | ClogP | MORV |
|---|---|---|---|---|---|
| 31 | 32388-55-9 | 1-((3R,3aR,7R,8aS)-3,6,8,8-tetramethyl-2,3,4,7,8,8a-hexahydro-1H-3a,7-methanoazulen-5-yl)ethan-1-one | 8.5E−05 | 4.97 | 4.49 |
| 32 | 167254-80-0 | 3,5,5,6,7,8,8-heptamethyl-5,6,7,8-tetrahydronaphthalene-2-carbonitrile | 6.9E−05 | 5.88 | 3.36 |
| 33 | 66072-32-0 | 4-(1,7,7-trimethyl-6-bicyclo[2.2.1]heptanyl)cyclohexan-1-ol | 3.0E−05 | 4.45 | 3.50 |
| 34 | 501929-47-1 | (E)-4-((3aR,4R,7R,7aR)-1,3a,4,6,7,7a-hexahydro-5H-4,7-methanoinden-5-ylidene)-3-methylbutan-2-ol | 8.5E−06 | 3.87 | 5.44 |
| 35 | 3681-73-0 | (E)-3,7-dimethylocta-2,6-dien-1-yl palmitate) | 3.0E−09 | 10.75 | 3.31 |
| 36 | 1222-05-5 | 1,3,4,6,7,8-hexahydro-4,6,6,7,8,8,-hexamethyl-cyclopenta[g]benzopyran | 4.14E−04 | 5.93 | 4.46 |
| 37 | 1392325-86-8 | 5H-Cyclopenta[h]quinazoline, 6,6a,7,8,9,9a-hexahydro-7,7,8,9,9-pentamethyl- | 2.92E−04 | 5.02 | 3.98 |
| 39 | 3407-42-9 | Cyclohexanol, 3-(5,5,6-trimethylbicyclo[2.2.1]hept-2-yl)- | 1.90E−05 | 4.40 | 3.95 |
| 41 | 6790-58-5 | Naphtho[2,1-b]furan,dodecahydro-3a,6,6,9a-tetramethyl-, (3aR,5aS, 9aS,9bR)- | 9.34E−03 | 5.11 | 3.06 |
| 42 | 68155-66-8 | Ethanone, 1-(1,2,3,5,6,7,8,8a-octahydro-2,3,8,8-tetramethyl-2-naphthalenyl)- | 5.65E−04 | 4.75 | 3.27 |
| 43 | 68155-67-9 | Ethanone, 1-(1,2,3,4,6,7,8,8a-octahydro-2,3,8,8-tetramethyl-2-naphthalenyl)- | 5.65E−04 | 5.19 | 3.23 |
| 44 | 68991-97-9 | 2-Naphthalenecarboxaldehyde,1,2,3,4,5,6,7,8-octahydro-8,8-dimethyl- | 4.36E−03 | 3.92 | 3.11 |
| 45 | 77-54-3 | 1H-3a,7-Methanoazulen-6-ol, octahydro-3,6,8,8-tetramethyl-, 6-acetate, (3R,3aS,6R,7R,8aS)- | 1.92E−03 | 5.31 | 4.69 |
| 46 | 472-97-9 | Tricyclo[6.3.1.02,5]dodecan-1-ol, 4,4,8-trimethyl-, (1R,2S,5R,8S)- | 1.63E−04 | 4.52 | 4.00 |
| 47 | 16223-63-5 | 1H-3a,6-Methanoazulene-3-methanol, octahydro-7,7-dimethyl-8-methylene-, (3S,3aR,6R,8aS)- | 4.40E−05 | 3.52 | 4.29 |
| 48 | 67801-36-9 | 1H-Indole-1-heptanol, η-1H-indol-1-yl-α,α,ε-trimethyl- | 8.72E−14 | 6.27 | 4.63 |

TABLE 3

List of materials with Sulfur MORV > 3; ClogP > 3 and VP > .005

| Number | CAS Number | Material Name | VP@ 25 C. (Torr) | ClogP | MORV |
|---|---|---|---|---|---|

TABLE 3-continued

List of materials with Sulfur MORV > 3; ClogP > 3 and VP > .005

| CAS Number | Number | Material Name | VP@ 25 C. (Torr) | ClogP | MORV |
|---|---|---|---|---|---|
| 6 | 116126-82-0 | Ethyl (1R,2R,3R,4R)-3-isopropylbicyclo[2.2.1]hept-5-ene-2-carboxylate | 1.2E−02 | 3.68 | 3.22 |
| 7 | 3738-00-9 | 3aR,5aR,9aR,9bR)-3a,6,6,9a-tetramethyldodecahydronaphtho[2,1-b]furan | 9.3E−03 | 5.11 | 3.06 |
| 8 | 33885-52-8 | (alpha,alpha,6,6-tetramethylbicyclo[3.1.1]hept-2-ene-propanal) | 6.9E−03 | 4.31 | 3.18 |
| 9 | 1139-30-6 | 4,5-epoxy-4,11,11-trimethyl-8-methylenebicyclo(7.2.0)undecane) | 6.7E−03 | 4.47 | 3.57 |
| 41 | 6790-58-5 | Naphtho[2,1-b]furan, dodecahydro-3a,6,6,9a-tetramethyl-, (3aR,5aS,9aS,9bR)- | 9.34E−03 | 5.11 | 3.06 |

The materials in Tables 1-7 may be supplied by one or more, but not limited to, the following:
Firmenich Inc. of Plainsboro N.J. USA; International Flavor and Fragrance Inc. New York, N.Y. USA; Takasago Corp. Teterboro, N.J. USA; Symrise Inc. Teterboro, N.J. USA; Sigma-Aldrich/SAFC Inc. Carlsbad, Calif. USA; V. Mane Fils 620, Route de Grasse 06620 Le-Bar-Sur-Loup France; and Bedoukian Research Inc. Danbury, Conn. USA.

In one aspect of said hair care composition, said composition comprises one or more perfume raw materials.

In one aspect of said hair care composition, said composition comprises a total of, based on total consumer product weight, from about 0.0001% to about 2% of one or more of a malodor reduction material; from about 0.0001% to about 0.5% of one or more of a malodor reduction material; from about 0.0002% to about 0.25% of a malodor reduction material; and from about 3% to 30% of a surfactant, and, optionally, a miscellar phase and/or lamellar phase.

In one aspect of said hair care composition, said composition comprises a total, based on total consumer product weight, of from about 0.1% to about 50% of a material selected from structurants, humectants, fatty acids, inorganic salts, antimicrobial agents, antimicrobial agents actives and mixtures thereof.

In one aspect of said hair care composition, said composition comprises an adjunct ingredient selected from the group consisting of clay mineral powders, pearl pigments, organic powders, emulsifiers, distributing agents, pharmaceutical active, topical active, preservatives, surfactants and mixtures thereof.

A method of controlling malodors comprising: contacting a situs comprising a malodor and/or a situs that will become malodorous with a hair care composition selected from the group consisting of the hair care compositions disclosed herein is disclosed.

In one aspect of said method, said situs comprises the head of hair and said contacting step comprises contacting said hair containing a malodor with a sufficient amount of present invention's hair care composition to provide said hair with a level of malodor reduction material at least 0.0001 mg of malodor reduction material per body or head of hair, may be from about 0.0001 mg of malodor reduction material per head of hair to about 5 mg of malodor reduction material per head of hair, may be from about 0.0002 mg of malodor reduction material per head of hair about 2 mg of malodor reduction material per body or head of hair, a further may be from about 0.002 mg of malodor reduction material per head of hair to about 0.5 mg of malodor reduction material per head of hair.

Sulfur

The hair care composition of the present invention may include sulfur. The sulfur which is suitable for use herein can be any form of elemental sulfur. Sulfur exists at room temperatures primarily as rhombic crystals. The two most prevalent ways of obtaining elemental sulfur are: precipitation from hydrogen sulfide, with one route coming from contamination in sour gas, via the Claus process and mining underground deposits using superheated water, known as the Frasch process. Other forms of sulfur, such as monoclinic crystalline sulfur, oligomeric or polymeric sulfur, are the normal primary forms which elemental sulfur assumes at certain higher temperature ranges. At room temperatures, these forms convert, or revert, to rhombic sulfur. The sulfur while being in elemental form may be sulfur which has been physically mixed with protective colloids such as gum arabic, clays, waxes, oils, activated carbon, zeolites, silica or dispersing agents such as surfactants or subjected to processing steps to modify its particle size or other physical property. Sulfur is available commercially in a variety of forms such as pellets, cakes, prills, colloidal, micronized, sublimed, precipitated, and commercial flour.

Sulfur may have a particle size distribution wherein 90% of the particles (D90) of from about 30 micron (μm) to about 250 micron (μm); Sulfur may have a particle size distribution wherein the D90 is from about 30 micron (μm) to about 200 micron (μm); Sulfur may have a particle size distribution wherein the D90 is from about 30 micron (μm) to about 150 micron (μm); Sulfur may have a particle size distribution wherein the D90 is from about 30 micron (μm) to about 100 micron (μm).

Sulfur may have a particle size distribution wherein 50% of the particles (D50) is from about 5 micron (μm) to about 150 micron (μm); Sulfur may have a particle size distribution wherein the D50 is from about 10 micron (μm) to about 100 micron (μm); Sulfur may have a particle size distribution wherein the D50 is from about 15 micron (μm) to about 75 micron (μm); Sulfur may have a particle size distribution wherein the D50 is from about 20 micron (μm) to about 50 micron (μm).

Sulfur may have a particle size distribution wherein 10% of the particles (D10) is from about 1 micron (μm) to about 25 micron (μm); Sulfur may have a particle size distribution wherein the D10 is from 5 micron (μm) to about 25 micron (μm); Sulfur may have a particle size distribution wherein the D10 is from about 10 microns (μm) to about 25 micron (μm); Sulfur may have a particle size distribution wherein the D10 is from about 18 micron (μm) to about 25 micron (p m).

Sulfur may be present in a ratio of D(90)/D(10) of from about 3 to about 100; Sulfur may be present in a ratio of D(90)/D(10) of from about 3 to about 50; Sulfur may be present in a ratio of D(90)/D(10) of from about 3 to about 10; Sulfur may be present in a ratio of D(90)/D(10) of from about 3 to about 4.

The sulfur may be present in an amount from about 0.01% to 10%, from about 0.1% to about 9%, from about 0.25% to 8%, and from about 0.5% to 6%.

Adjunct Materials

While not essential for the purposes of the present invention, the non-limiting list of adjuncts illustrated hereinafter are suitable for use in the instant compositions and may be desirably incorporated in certain aspects of the invention, for example to assist or enhance performance, A variety of optional ingredients can also be added to hair care compositions. Optional ingredients can include, but are not limited to, structurants, humectants, fatty acids, inorganic salts, and other antimicrobial agents or actives.

A hair care composition can also include hydrophilic structurants such as carbohydrate structurants and gums. Some suitable carbohydrate structurants include raw starch (corn, rice, potato, wheat, and the like) and pregelatinized starch. Some suitable gums include carregeenan and xanthan gum. A hair care composition can include from about 0.1% to about 30%, from about 2% to about 25%, or from about 4% to about 20%, by weight of the hair care composition, of a carbohydrate structurant.

A hair care composition can also include one or more humectants. Examples of such humectants can include polyhydric alcohols. Further, humectants such as glycerin can be included the hair care composition as a result of production or as an additional ingredient. For example, glycerin can be a by-product after saponification of the hair care composition. Including additional humectant can result in a number of benefits such as improvement in hardness of the hair care composition, decreased water activity of the hair care composition, and reduction of a weight loss rate of the hair care composition over time due to water evaporation.

A hair care composition can include inorganic salts. Inorganic salts can help to maintain a particular water content or level of the hair care composition and improve hardness of the hair care composition. The inorganic salts can also help to bind the water in the hair care composition to prevent water loss by evaporation or other means. A hair care composition can optionally include from about 0.01% to about 15%, from about 1% to about 12%, or from about 2.5% to about 10.5%, by weight of the hair care composition, of inorganic salt. Examples of suitable inorganic salts can include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

A hair care composition can include one or more additional antibacterial agents that can serve to further enhance antimicrobial effectiveness of the hair care composition. A hair care composition can include, for example, from about 0.001% to about 2%, from about 0.01% to about 1.5%, or from about 0.1% to about 1%, by weight of the hair care composition, of additional antibacterial agent(s). Examples of suitable antibacterial agents can include carbanilides, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid, and other organic acids. Other suitable antibacterial agents are described in U.S. Pat. No. 6,488,943.

Scalp Active Material

In the present invention, the hair care composition may comprise a scalp active material, which may be an anti-dandruff active. The anti-dandruff active may be selected from the group consisting of: pyridinethione salts; zinc carbonate; azoles, such as ketoconazole, econazole, and elubiol; selenium sulfide; particulate sulfur; colloidal sulfur, keratolytic agents such as salicylic acid; and mixtures thereof. The anti-dandruff active may be an anti-dandruff particulate. The anti-dandruff particulate is a pyridinethione salt. Such anti-dandruff particulate should be physically and chemically compatible with the components of the composition, and should not otherwise unduly impair product stability, aesthetics or performance.

In the present invention, the sulfur or selenium sulfide may be present in an amount from about 0.01% to 10%, from about 0.1% to about 9%, from about 0.25% to 8%, and from about 0.5% to 6%.

Pyridinethione particulates are suitable particulate anti-dandruff actives for use in composition of the present invention. In the present invention, the anti-dandruff active may be a 1-hydroxy-2-pyridinethione salt and is in particulate form. In the present invention, the concentration of pyridinethione anti-dandruff particulate may range from about 0.01% to about 5%, by weight of the composition, or from about 0.1% to about 3%, or from about 0.1% to about 2%. In the present invention, the pyridinethione salts may be those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"; zinc pyrithione), commonly 1-hydroxy-2-pyridinethione salts in platelet particle form. In the present invention, the 1-hydroxy-2-pyridinethione salts may be in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. No. 2,809,971; U.S. Pat. Nos. 3,236,733; 3,753,196; 3,761,418; 4,345,080; 4,323,683; 4,379,753; and 4,470,982.

In the present invention, in addition to the anti-dandruff active selected from polyvalent metal salts of pyrithione, the composition may further comprises one or more anti-fungal and/or anti-microbial actives. In the present invention, the anti-microbial active may be selected from the group consisting of: coal tar, sulfur, charcoal, whitfield's ointment, castellani's paint, aluminum chloride, gentian violet, octopirox (piroctone olamine), ciclopirox olamine, undecylenic acid and its metal salts, potassium permanganate, selenium sulfide, sodium thiosulfate, propylene glycol, oil of bitter orange, urea preparations, azoxystrobin, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In present invention, the anti-microbial may be selected from the group consisting of: itraconazole, ketoconazole, selenium sulfide, coal tar, and mixtures thereof.

In the present invention, the azole anti-microbials may be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the composition, the azole anti-microbial active is included in an amount of from about 0.01% to about 5%, or from about 0.1% to about 3%, or from about 0.3% to about 2%, by total weight of the composition. In the present invention, the azole anti-microbial active may be ketoconazole. In the present invention, the sole anti-microbial active may be ketoconazole.

The present invention may also comprise a combination of anti-microbial actives. In the present invention, the combination of anti-microbial active may be selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In the present invention, the composition may comprise an effective amount of a zinc-containing layered material. In the present invention, the composition may comprise from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In the present invention, the ZLM may be selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In the present invention, the ZLM may be a layered double hydroxide conforming to the formula $[M^{2+}_{1-x}M^{3+}_{x}(OH)_2]^{x+}A^{m-}_{x/m}\cdot nH_2O$ wherein some or all of the divalent ions ($M^{2+}$) are zinc ions (Crepaldi, E L, Pava, P C, Tronto, J, Valim, J B J. *Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In the present invention, the ZLM may be a hydroxy double salt conforming to the formula $[M^{2+}_{1-x}M^{2+}_{1+x}(OH)_{3(1-y)}]^+ A^{n-}_{(1-3y)/n}\cdot nH_2O$ where the two metal ions ($M^{2+}$) may be the same or different. If they are the same and represented by zinc, the formula simplifies to $[Zn_{1+x}(OH)_2]^{2x+}2\times A^-\cdot nH_2O$. This latter formula represents (where x=0.4) materials such as zinc hydroxychloride and zinc hydroxynitrate. In the present invention, the ZLM may be zinc hydroxychloride and/or zinc hydroxynitrate. These are related to hydrozincite as well wherein a divalent anion replace the monovalent anion. These materials can also be formed in situ in a composition or in or during a production process.

In the present invention, the composition may comprise basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

The present invention may have a zinc-containing layered material and a pyrithione or polyvalent metal salt of pyrithione, wherein the ratio of zinc-containing layered material to pyrithione or a polyvalent metal salt of pyrithione is from about 5:100 to about 10:1, or from about 2:10 to about 5:1, or from about 1:2 to about 3:1.

Hair Care Compositions

Exemplary hair care rinse-off hair care compositions can include an aqueous carrier, which can be present at a level of from about 5% to about 95%, or from about 60% to about 85%. The aqueous carrier may comprise water, or a miscible mixture of water and organic solvent. Non-aqueous carrier materials can also be employed.

In the present invention, a surfactant may be present in the range of about 0.1% to about 40%, may be from about 0.5% to about 30%, may be from about 1% to about 25%.

Such rinse-off hair care compositions can include one or more detersive surfactants. The detersive surfactant component can be included to provide cleaning performance to the product. The detersive surfactant component in turn comprises anionic detersive surfactant, zwitterionic or amphoteric detersive surfactant, or a combination thereof. A representative, non-limiting, list of anionic surfactants includes anionic detersive surfactants for use in the compositions can include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the anionic surfactant can be sodium lauryl sulfate or sodium laureth sulfate. The concentration of the anionic surfactant component in the product can be sufficient to provide a desired cleaning and/or lather performance, and generally ranges from about 2% to about 40%.

Amphoteric detersive surfactants suitable for use in the rinse-off hair care compositions are well known in the art, and include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic detersive surfactants suitable for use in the rinse-off hair care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include betaines, including cocoamidopropyl betaine.

In the present invention, the hair care composition may comprise a cationic surfactant.

The liquid rinse off hair care composition can comprise one or more phases. Such hair care compositions can include a cleansing phase and/or a benefit phase (i.e., a single- or multi-phase composition). Each of a cleansing phase or a benefit phase can include various components. The cleansing phase and the benefit phase can be blended, separate, or a combination thereof. The cleansing phase and the benefit phase can also be patterned (e.g. striped).

The cleansing phase of a hair care composition can include at least one surfactant. The cleansing phase can be an aqueous structured surfactant phase and constitute from about 5% to about 20%, by weight of the hair care composition. Such a structured surfactant phase can include sodium trideceth(n) sulfate, hereinafter STnS, wherein n can define average moles of ethoxylation. n can range, for example, from about 0 to about 3; from about 0.5 to about 2.7, from about 1.1 to about 2.5, from about 1.8 to about 2.2, or n can be about 2. When n can be less than 3, STnS can provide improved stability, improved compatibility of benefit agents within the hair care compositions, and increased mildness of the compositions as disclosed in U.S. Pre-Grant Publication No. 2010/009285 A1.

The cleansing phase can also comprise at least one of an amphoteric surfactant and a zwitterionic surfactant. Suitable amphoteric or zwitterionic surfactants (in addition to those cited herein) can include, for example, those described in U.S. Pat. Nos. 5,104,646 and 5,106,609.

A cleansing phase can comprise a structuring system. A structuring system can comprise, optionally, a non-ionic emulsifier, optionally, from about 0.05% to about 5%, by weight of the hair care composition, of an associative polymer; and an electrolyte.

The hair care composition can optionally be free of sodium lauryl sulfate, hereinafter SLS, and can comprise at least a 70% lamellar structure. However, the cleansing phase could comprise at least one surfactant, wherein the at least one surfactant includes SLS. Suitable examples of SLS are described in U.S. Pre-Grant Publication No. 2010/0322878 A1.

Rinse-off hair care compositions can also include a benefit phase. The benefit phase can be hydrophobic and/or anhydrous. The benefit phase can also be substantially free of surfactant. A benefit phase can also include a benefit agent. In particular, a benefit phase can comprise from about 0.1% to about 50% benefit agent by weight of the hair care composition. The benefit phase can alternatively comprise less benefit agent, for example, from about 0.5% to about 20% benefit agent, by weight of the hair care composition. Examples of suitable benefit agents can include petrolatum, glyceryl monooleate, mineral oil, natural oils, and mixtures thereof. Additional examples of benefit agents can include water insoluble or hydrophobic benefit agents. Other suitable benefit agents are described in U.S. Pre-Grant Publication No. 2012/0009285 A1.

Non-limiting examples of glycerides suitable for use as hydrophobic hair benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic hair benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic hair benefit agents herein can include decaglyceryl distearate, decaglyceryl diisostearate, decaglyceryl monomyriate, decaglyceryl monolaurate, hexaglyceryl monooleate, and combinations thereof.

Rinse-Off Conditioner Composition

The conditioner composition described herein comprises a sum of total 0.0001% to about 2% of a malodor reduction material and one or more malodor reduction materials having a Sulfur MORV>3; b) from about 0.01% to about 10% of sulfur; and from about 0.1% to about 10% of a cationic surfactant or a mixture of cationic surfactants and an aqueous carrier. The conditioner composition may also comprise a conditioner gel matrix comprising part or all of the cationic surfactant, whereas the conditioner gel network may also comprise one or more high melting point fatty compounds (i.e. fatty alcohols), and a second aqueous carrier.

The conditioner gel matrix of the conditioner composition includes a cationic surfactant or a cationic surfactant system. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt. The cationic surfactant system can be included in the composition at a level by weight of from about 0.1% to about 10%, from about 0.5% to about 8%, from about 0.8% to about 5%, and from about 1.0% to about 4%.

The conditioner gel matrix of the conditioner composition includes one or more high melting point fatty compounds. Suitable fatty alcohols include, for example, cetyl alcohol, stearyl alcohol, behenyl alcohol, and mixtures thereof. The high melting point fatty compound can be included in the conditioner composition at a level of from about 0.1% to about 20%, alternatively from about 1% to about 15%, and alternatively from about 1.5% to about 8% by weight of the composition. The conditioner gel matrix of the conditioner composition includes a second aqueous carrier. The second aqueous carrier may comprise water, or a miscible mixture of water and organic solvent.

Leave-on Treatment Composition

The leave-on treatment composition described herein comprises a sum of total 0.0001% to about 2% of a malodor reduction material and one or more malodor reduction materials having a Sulfur MORV>3; b) from about 0.01% to about 10% of sulfur and from about 0.1% to about 10% of a cationic surfactant or a mixture of cationic surfactants and an aqueous carrier.

The leave-on treatment may also comprise one or more rheology modifiers and a third aqueous carrier.

In the present invention, the leave-on treatment may include a conditioner gel matrix as described above (in the rinse-off conditioner description).

In the present invention, the leave-on treatment may include one or more rheology modifiers. Any suitable rheology modifier can be used. In the present invention, the leave-on treatment may comprise from about 0.01% to about 3% of a rheology modifier, alternatively from about 0.1% to about 1% of a rheology modifier, Additional Components The conditioner compositions, and/or leave-on treatments described herein may optionally comprise one or more additional components known for use in hair care or personal care products, Non-limiting examples of additional components for use in the hair care compositions include conditioning agents (silicone or non-silicone conditioning agents), natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

The rinse-off hair care composition can be applied by a variety of means, including by rubbing, wiping or dabbing with hands or fingers, or by means of an implement and/or delivery enhancement device. Non-limiting examples of implements include a sponge or sponge-tipped applicator, a mesh shower puff, a swab, a brush, a wipe (e.g., wash cloth), a loofah, and combinations thereof. Non-limiting examples of delivery enhancement devices include mechanical, electrical, ultrasonic and/or other energy devices. Employment of an implement or device can help delivery of the particulate antimicrobial agent to target regions, such as, for example, hair follicles and undulations that can exist in the underarm. The rinse-off care product can be sold together with such an implement or device. Alternatively, an implement or device can be sold separately but contain indicium to indicate usage with a rinse-off care product. Implements and delivery devices can employ replaceable portions (e.g., the skin interaction portions), which can be sold separately or sold together with the rinse-off care product in a kit.

Test Methods

Malodor reduction materials may be separated from mixtures, including but not limited to finished products such as consumer products and identified, by analytical methods that include GC-MS and/or NMR.

Test Method for Determining Saturation Vapour Pressure (VP@25C)

The saturation Vapour Pressure (VP) values are computed for each perfume raw material (PRM) in the perfume mixture being tested. The VP of an individual PRM is calculated using the VP Computational Model, version 14.02 (Linux) available from Advanced Chemistry Development Inc. (ACD/Labs) (Toronto, Canada) to provide the VP value at 25° C. expressed in units of torr. The ACD/Labs' Vapor Pressure model is part of the ACD/Labs model suite.

Test Method for Determining the Logarithm of the Octanol/Water Partition Coefficient (C log P)

The value of the log of the Octanol/Water Partition Coefficient (log P) is computed for each PRM in the perfume mixture being tested. The Clog P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Test Method for the Generation of Molecular Descriptors

In order to conduct the calculations involved in the computed-value test methods described herein, the starting information required includes the identity, weight percent, and molar percent of each PRM in the perfume being tested, as a proportion of that perfume, wherein all PRMs in the perfume composition are included in the calculations. Additionally for each of those PRMs, the molecular structure, and the values of various computationally-derived molecular descriptors are also required, as determined in accordance with the Test Method for the Generation of Molecular Descriptors described herein.

For each PRM in a perfume mixture or composition, its molecular structure is used to compute various molecular descriptors. The molecular structure is determined by the graphic molecular structure representations provided by the Chemical Abstract Service ("CAS"), a division of the American Chemical Society, Columbus, Ohio, U.S.A. These molecular structures may be obtained from the CAS Chemical Registry System database by looking up the index name or CAS number of each PRM. For PRMs, which at the time of their testing are not yet listed in the CAS Chemical Registry System database, other databases or information sources may be used to determine their structures. For a PRM which has potentially more than one isomer present, the molecular descriptor computations are conducted using the molecular structure of only one of the isomers, which is selected to represent that PRM. The selection of isomer is determined by the relative amount of extension in the molecular structures of the isomers. Of all the isomers of a given PRM, it is the isomer whose molecular structure that is the most prevalent which is the one that is selected to represent that PRM. The structures for other potential isomers of that PRM are excluded from the computations. The molecular structure of the isomer that is the most prevalent is paired with the concentration of that PRM, where the concentration reflects the presence of all the isomers of that PRM that are present.

A molecule editor or molecular sketching software program, such as ChemDraw (CambridgeSoft/PerkinElmer Inc., Waltham, Mass., U.S.A.), is used to duplicate the 2-dimensional molecular structure representing each PRM. Molecular structures should be represented as neutral species (quaternary nitrogen atoms are allowed) with no disconnected fragments (e.g., single structures with no counter ions). The winMolconn program described below can convert any deprotonated functional groups to the neutral form by adding the appropriate number of hydrogen atoms and will discard the counter ion.

For each PRM, the molecular sketching software is used to generate a file which describes the molecular structure of the PRM. The file(s) describing the molecular structures of the PRMs is subsequently submitted to the computer software program winMolconn, version 1.0.1.3 (Hall Associates Consulting, Quincy, Mass., U.S.A., www.molconn.com), in order to derive various molecular descriptors for each PRM. As such, it is the winMolconn software program which dictates the structure notations and file formats that are acceptable options. These options include either a MACCS SDF formatted file (i.e., a Structure-Data File); or a Simplified Molecular Input Line Entry Specification (i.e., a SMILES string structure line notation) which is commonly used within a simple text file, often with a ".smi" or ".txt" file name extension. The SDF file represents each molecular structure in the format of a multi-line record, while the syntax for a SMILES structure is a single line of text with no white space. A structure name or identifier can be added to the SMILES string by including it on the same line following the SMILES string and separated by a space, e.g.: C1=CC=CC=C1 benzene.

The winMolconn software program is used to generate numerous molecular descriptors for each PRM, which are then output in a table format. Specific molecular descriptors derived by winMolconn are subsequently used as inputs (i.e., as variable terms in mathematical equations) for a variety of computer model test methods in order to calculate values such as: saturation Vapour Pressure (VP); Boiling Point (BP); logarithm of the Octanol/Water Partition Coefficient (log P); Odour Detection Threshold (ODT); Malodour Reduction Value (MORV); and/or Universal Malodour Reduction Value (Universal MORV) for each PRM. The molecular descriptor labels used in the models' test method computations are the same labels reported by the winMolconn program, and their descriptions and definitions can be found listed in the winMolconn documentation. The following is a generic description of how to execute the winMolconn software program and generate the required molecular structure descriptors for each PRM in a composition.

Computing Molecular Structure Descriptors using winMolconn:

1) Assemble the molecular structure for one or more perfume ingredients in the form of a MACCS Structure-Data File, also called an SDF file, or as a SMILES file.
2) Using version 1.0.1.3 of the winMolconn program, running on an appropriate computer, compute the full complement of molecular descriptors that are available from the program, using the SDF or SMILES file described above as input.
   a. The output of winMolconn is in the form of an ASCII text file, typically space delimited, containing the structure identifiers in the first column and respective molecular descriptors in the remaining columns for each structure in the input file.
3) Parse the text file into columns using a spreadsheet software program or some other appropriate technique. The molecular descriptor labels are found on the first row of the resulting table.
4) Find and extract the descriptor columns, identified by the molecular descriptor label, corresponding to the inputs required for each model.
   a. Note that the winMolconn molecular descriptor labels are case-sensitive.

MORV Calculation

1.) Input Molecular Descriptor values as determined via the method above into the following equation:

$$MORV = -0.0035 + 0.8028 \times (SHCsatu) + 2.1673 \times (xvp7) - 1.3507 \times (c1C1C3d) + 0.61496 \times (c1C1O2) + 0.00403 \times (idc) - 0.23286 \times (nd2).$$

This equation relates a material's effectiveness in reducing the malodor 3-mercapto-3-methylhexan-1-ol (thiol based malodors) and in the present invention it is used it as a marker of other sulfur odor compounds like hydrogen sulfide and methanethiol.

2.) For purpose of the present application, a material's MORV is the highest MORV value from the above equation.

The purpose of this experimental design is to determine whether malodor reducing compositions show benefit in reducing the perception of malodor from sulfur-containing shampoos.

Sensory Test Method:

A hair switch is rinsed thoroughly with water (38C) to thoroughly wet the switch (5-10 seconds). 0.1 g of Test product is added per gram of hair, and lather for 20 seconds. At 20 seconds, water is added and lathering is continued to 30 seconds. The hair switch is assessed for sulfur malodor (SM-1). The hair switch is completely rinsed. The hair switch is assessed for sulfur malodor (SM-2). The hair switch is gently dired of excess water with a towel. The hair switch is blowed dried on high heat setting until completely dry to the touch. The hair switch is immediately assessed for sulfur malodor (SM-3). The hair switch is cooled for 3-5 minutes (until cool to the touch). The hair switch is assessed for sulfur malodor (SM-4). SM-1, SM-2, SM-3 and SM-4 are added together to obtain the total sulfur malodor (TSM) or cumulative sulfur odor.

In the present invention, the sulfur malodor may be assessed or measured on a scale of 0 (no malodor) to 9 (severe malodor). A non-limiting example of a malodor assessment may be as follows: Malodor Assessment Scale 10-point scale with descriptors: 0=None No fragrance/malodour present; 1=Slight I think there is fragrance/malodour present (unsure); 2=Slight to moderate I detect something, but can I recognize it?; 3=Moderate Slight fragrance/malodour present; 4=Moderate to high Moderate fragrance/malodour present; 5=High; 6=High to Very High; 7=Very high Strong fragrance/malodour present; 8=Extremely High; 9=Extremely High+Extremely strong fragrance/malodour present.

TABLE 4

Sulfur malodor reduction materials selected for testing (Group 1, Sulfur MORV > 3)

| CAS | Material Name | VP@ 25 C. torr | CLogP | Sulfur MORV |
| --- | --- | --- | --- | --- |
| 476332-65-7 | (2,2,6,6,7,8,8-heptamethyldecahydro-2H-indeno[4,5-b]furan | 3.23E−03 | 6.14 | 5.66 |
| 67801-36-9 | 1H-Indole-1-heptanol, η-1H-indol-1-yl-α,α,ε-trimethyl- | 8.72E−14 | 6.27 | 4.63 |
| 211299-54-6 | 4aR,5R,7aS,9R)-2,2,5,8,8,9a-hexamethyloctahydro-4H-4a,9-methanoazuleno[5,6-d][1,3]dioxole | 1.8E−03 | 4.85 | 6.82 |
| 5986-55-0 | 1,6-Methanonaphthalen-1(2H)-ol, octahydro-4,8a,9,9-tetramethyl-, (1R,4S,4aS,6R,8aS)- | 2.78E−04 | 4.46 | 4.34 |

TABLE 5

Sulfur malodor reduction materials selected for testing (Group 2, Decanal and other aldehydes)

| CAS | Material Name | VP@ 25 C. torr | CLogP | Sulfur MORV |
| --- | --- | --- | --- | --- |
| 112-31-2 | Decanal | 2.07E−01 | 4.25 | −0.44 |
| 112-45-8 | undec-10-enal | 3.90E−02 | 3.97 | −0.08 |
| 111998-18-6 | 6-cycloentylidene-Hexanal | 1.82E−02 | 3.47 | 0.85 |
| 141-13-9 | 2,6, 10-Trimethylundec-9-enal | 2.57E−03 | 5.17 | −0.66 |
| 300371-33-9 | 3-(3,3-dimethyl-12-dihydroinden-5-yl)propanal | 3.92E−03 | 4.01 | 2.20 |
| 30390-51-3 | 4-Dodecenal | 1.55E−02 | 4.86 | 0.44 |
| 65405-70-1 | Dec-4-enal | 3.31E−01 | 3.60 | 0.31 |
| 106-72-9 | 2,6-Dimethylhept-5-enal | 6.22E−01 | 3.14 | −1.38 |
| 2385-77-5 | 3,7-dimethyloct-6-enal | 2.15E−01 | 3.44 | −1.42 |
| 7775-00-0 | 3-(4-propan-2-ylphenyl)propanal | 1.82E−02 | 3.32 | 1.46 |
| 121-32-4 | 3-Ethoxy-4-hydroxybenzaldehyde | 8.84E−04 | 1.59 | −0.56 |

TABLE 6

Sulfur malodor reduction material selected for testing (group 3, ketones, esters and alcohol)

| CAS | Material Name | VP@ 25 C. torr | CLogP | Sulfur MORV |
| --- | --- | --- | --- | --- |
| 56973-85-4 | 1-(5,5-dimethyl-1-cyclohexenyl)pent-4-en-1-one | 7.63E−03 | 4.01 | 2.17 |
| 7388-22-9 | 3-Buten-2-one, 4-(2,2-dimethyl-6-methylenecyclohexyl)-3-methyl | 2.72E−03 | 3.84 | 0.11 |
| 117-98-6 | 6-Azulenol, 1,2,3,3a,4,5,6,8a-octahydro-4,8-dimethyl-2-(1-methylethylidene)-, 6-acetate | 1.20E−04 | 5.23 | 2.06 |
| 3289-28-9 | Ethyl cyclohexanecarboxylate | 3.85E−01 | 3.01 | −0.04 |
| 67859-96-5 | (335-trimethylcyclohexyl) acetate | 1.99E−01 | 4.03 | −0.70 |
| 65405-72-3 | 1-Naphthalenol, 1,2,3,4,4a,7,8,8a-octahydro-2,4a,5,8a-tetramethyl-, 1-formate | 2.36E−03 | 4.69 | 1.24 |

TABLE 6-continued

Sulfur malodor reduction material selected for testing (group 3, ketones, esters and alcohol)

| CAS | Material Name | VP@ 25 C. torr | CLogP | Sulfur MORV |
|---|---|---|---|---|
| 198404-98-7 | [(1R2S)-1-methyl-2-[[(1R3S5S)-122-trimethyl-3-bicyclo[3.1.0]hexanyl]methyl]cyclopropyl]methanol | 9.02E−04 | 4.37 | 2.86 |
| 1913285-57-0 | 6-Octen-1-ol, 2,4,7-trimethyl- | 1.31E−02 | 3.80 | −1.35 |
| 70788-30-6 | Cyclohexanepropanol, 2,2,6-trimethyl-α-propyl- | 2.97E−03 | 3.14 | 0.39 |
| 118562-73-5 | Cyclododecaneethanol, β-methyl- | 1.80E−05 | 5.45 | 0.77 |
| 139539-66-5 | 6-Oxabicyclo[3.2.1]octane, 5-methyl-1-(2,2,3-trimethyl-3-cyclopenten-1-yl)- | 3.81E−03 | 4.68 | 1.79 |
| 950-33-4 | Cyclododecane, 1,1-dimethoxy- | 3.09E−03 | 4.61 | 1.40 |
| 4602-84-0 | 2,6,10-Dodecatrien-1-ol, 3,7,11-trimethyl- | 3.70E−04 | 4.72 | −1.09 |
| 111-80-8 | 2-Nonynoic acid, methyl ester | 5.68E−02 | 3.49 | −0.18 |
| 28069-72-9 | 2,6-Nonadien-1-ol, (2E,6Z)- | 5.37E−02 | 2.53 | 0.70 |
| 76649-25-7 | 3,6-Nonadien-1-ol | 3.36E−02 | 2.52 | 0.20 |

TABLE 7

Sulfur malodor reduction material selected for testing (Group 4-Patchouli and Derivatives and Clear Wood ®) Clear Wood ® under CAS 1450625-49-6 with a primary chemical name: Oils, Patchouli, patchoulol synthase-modified *Saccharomyces cerevisiae*-fermented, from carbohydrates. Additional description of the Clear Wood material is found at this source and incorporated herein by reference: http://www.firmenich.com/sites/default/files/uploads/files/ingredients/marketing-sheet/perfumery/CLEARWOOD_970953.pdf

| No. | Material Name | CAS # | Example Supplier |
|---|---|---|---|
| 1 | Patchouli oil MD | EC number: 939-227-3 | Reynaud &Fils |
| 2 | Patchouli oil Indonesia | 84238-39-1, 8014-09-3 | IFF |
| 3 | Patchouli 30 | 8014-09-3 | Reynaud &Fils |
| 4 | Clear Wood ® | 1450625-49-6 | Firmenich |

TABLE 8

Sulfur malodor reduction material selected for testing (Group 5-Mint oils and select mint components)

| No. | Material Name | CAS# | Example Supplier |
|---|---|---|---|
| 1 | Peppermint oil mixture | 8006-90-4 primary constituent | IP Callison |
| 2 | Peppermint oil | 8006-90-4, 84082-70-2 | Ungerer |
| 3 | Mint Piperita Cascade SX | 8006-90-4 | Firmenich |
| 4 | Mint Spicata Terpeneless SX | 68917-46-4 | Firmenich |
| 5 | Mint Spicata FW Native | 8008-79-5 | Firmenich |
| 6 | Spearmint | 8008-79-5 | Mane |
| 7 | L-Carvone | 99-49-0 | Global Essence |
| 8 | L-Menthol | 2216-51-5 | Symrise |

Results

TABLE 9

Results for sulfur malodor reduction material selected for testing—Group 1

| CAS | Material Name | Adding water | Rinse Wet Hair | Blow Dried Hot Hair | Cooled Dry Hair | Cumulative sulfur score | Use comments |
|---|---|---|---|---|---|---|---|
|  | Sulfur free shampoo reference * | 0 | 0 | 0 | 0 | 0 | no sulfur odor |
|  | Shampoo reference containing 2% Sulfur and no perfume ** | 3 | 1 | 2 | 1 | 7 | matches, slight onion, slight gassy |

TABLE 9-continued

Results for sulfur malodor reduction material selected for testing—Group 1

| CAS | Material Name | Adding water | Rinse Wet Hair | Blow Dried Hot Hair | Cooled Dry Hair | Cumulative sulfur score | Use comments |
|---|---|---|---|---|---|---|---|
| 476332-65-7 | (2,2,6,6,7,8,8-heptamethyldecahydro-2H-indeno[4,5-b]furan | 0 | 0 | 0 | 0 | 0 | No sulfur, high amber, |
| 67801-36-9 | 1H-Indole-1-heptanol, η-1H-indol-1-yl-α,α,ϵ-trimethyl- | 0 | 0 | 1 | 0 | 1 | Floral no sulfur |

* Sulfur Free Shampoo Reference is a commercially marketed antidandruff shampoo formulation containing ZPT, fragrance, and Peppermint oil mixture.
** Shampoo reference containing 2% Sulfur and no perfume is representative of Example 1 (Shampoo Examples herein) with no neat fragrance.

Materials in this group (Group 1, MORV>3) have met success criteria wherein the cumulative sulfur score are lower than 2. In the present invention, success criteria may be a cumulative sulfur score of 0 to 2, In the present invention, the MORV may be a MORV>3; it may be a MORV>3.2; it may be a MORV>3.5.

TABLE 10

Results for sulfur malodor reduction materials selected for testing—Group 2—Decanal and other aldehydes

| CAS | Material Name | Adding water | Rinse Wet Hair | Blow Dried Hot Hair | Cooled Dry Hair | Cumulative sulfur score | Use comments |
|---|---|---|---|---|---|---|---|
| 112-31-2 | Decanal | 1 | 0 | 1 | 0 | 2 | slight mineral, slight onion |
| 112-45-8 | undec-10-enal | 1 | 0 | 1 | 0 | 2 | slight mineral, slight onion |
| 111998-18-6 | 6-cyclopentylidene-Hexanal | 1 | 0 | 1 | 0 | 2 | slight onion, slight matches |
| 141-13-9 | 2,6,10-Trimethylundec-9-enal | 0 | 0 | 0 | 0 | 0 | no sulfur odor |
| 300371-33-9 | 3-(3,3-dimethyl-12-dihydroinden-5-yl)propanal | 0 | 0 | 1 | 0 | 1 | very slight onion |
| 106-72-9 | 2,6-Dimethylhept-5-enal | 2 | 1 | 1 | 0 | 4 | mineral, onion |
| 2385-77-5 | 3,7-dimethyloct-6-enal | 3 | 1 | 2 | 1 | 7 | onion, slight gassy |
| 7775-00-0 | 3-(4-propan-2-ylphenyl)propanal | 2 | 0 | 1 | 0 | 3 | slight onion |

Decyl aldehyde and several other aldehydes in this group (Group 2) including undec-10-enal, 6-cyclopentylidene-Hexanal, 2,6,10-Trimethylundec-9-enal, 3-(3,3-dimethyl-12-dihydroinden-5-yl)propanal, 4-Dodecenal, Dec-4-enal have met success criteria wherein the cumulative sulfur score are from 2 to 0. They are effective sulfur malodor reduction materials.

TABLE 11

Results for sulfur malodor reduction materials selected for testing—Group 3—ketones, esters and alcohols

| CAS | Material Name | Adding water | Rinse Wet Hair | Blow Dried Hot Hair | Cooled Dry Hair | Cumulative sulfur score | Use comments |
|---|---|---|---|---|---|---|---|
| 56973-85-4 | 1-(5,5-dimethyl-1-cyclohexenyl)pent-4-en-1-one | 0 | 1 | 2 | 2 | 5 | Onion, pineapple |
| 7388-22-9 | 3-Buten-2-one, 4-(2,2-dimethyl-6-methylenecyclohexyl)-3-methyl- | 0 | 1 | 3 | 0 | 4 | Berry, onion |
| 1913285-57-0 | 6-Octen-1-ol, 2,4,7-trimethyl- | | 1 | 2 | 1 | 7 | gassy |
| 67859-96-5 | (335-trimethylcyclohexyl) acetate | | 0 | 2 | 0 | 4 | mineral, slight gassy |
| 117-98-6 | 6-Azulenol, 1,2,3,3a,4,5,6,8a-octahydro-4,8-dimethyl-2-(1-metlaylethylidene)-, 6-acetate | | 1 | 1 | 1 | 4 | slight onion |
| 198404-98-7 | [(1R2S)-1-methyl-2-[[1R3S5S)-122-trimethyl-3-bicyclo[3.1.0]hexanyl]methyl]cyclopropyl]methanol | 1 | 0 | 1 | 0 | 2 | slight matchy creamy sandalwood |
| 3289-28-9 | Ethyl cyclohexanecarboxylate | | 0 | 1 | 0 | 2 | very diffusive apple/pineapple slight onion |
| 70788-30-6 | Cyclohexanepropanol, 2,2,6-trimethyl-α-propyl- | 1 | 1 | 1 | 0 | 3 | Amber wood |

Several materials in this group (Group 3—Ketones, esters and alcohols) have cumulative sulfur scores from 4 and higher and they are not effective sulfur malodor reduction. [(1R2S)-1-methyl-2-[[(1R3S5S)-122-trimethyl-3-bicyclo[3.1.0]hexanyl]methyl]cyclopropyl]methanol, Cyclohexanepropanol, 2,2,6-trimethyl-α-propyl, -and Ethyl cyclohexanecarboxylate have met success criteria and have a cumulative sulfur score of less than 3 or lower. They are effective sulfur malodor reduction materials.

TABLE 12

Results for sulfur malodor reduction materials selected for testing—Group 4—Patchouli Oils

| No. | Material Name | CAS | Example Supplier | Adding water | Rinse Wet Hair | Blow Dried Hot Hair | Cooled Dry Hair | Cumulative sulfur score | Use comments |
|---|---|---|---|---|---|---|---|---|---|
| 1 | Patchouli oil MD | EC number: 939-227-3 | Reynaud &Fils | 0 | 0 | 0 | 0 | 0 | no sulfur odor |
| 2 | Patchouli Indonesia | 84238-39-1, 8014-09-3 | IFF | 0 | 0 | 0 | 0 | 0 | no sulfur odor |
| 3 | Patchouli 30 | 8014-09-3 | Reynaud &Fils | 0 | 0 | 0 | 0 | 0 | no sulfur odor |
| 4 | Clear Wood® | 1450625-49-6 | Firmenich | 0 | 0 | 0 | 0 | 0 | no sulfur odor |

The patchouli oils are very effective for reducing sulfur malodor and met success criteria with the cumulative sulfur score of 0.

TABLE 13

Results for sulfur malodor reduction materials selected for testing—Group 5 (Mint oil and select mint components)

| Material No. | Material Name | Adding water | Rinse Wet Hair | Blow Dried Hot Hair | Cooled Dry Hair | Cumulative sulfur score | Use comments |
|---|---|---|---|---|---|---|---|
| 1 | Peppermint oil mixture (0.02% net mint) | 1 | 0 | 1 | 0 | 2 | Slight onion |
| 2 | Peppermint oil (0.075%) | 1 | 0 | 2 | 1 | 4 | Onion, licorice |
| 3 | Mint Piperita Cascade SX (0.02% net mint) | 1 | 0 | 1 | 0 | 2 | Slight onion |
| 4 | Mint Spicata Terpeneless SX (0.02% net mint) | 0 | 0 | 0 | 0 | 0 | No sulfur |
| 5 | Mint Spicata FW Native (0.075% net mint) | 2 | 0 | 2 | 0 | 4 | Onion, minty |
| 6 | Spearmint 0.075% net mint) | 2 | 0 | 1 | 0 | 3 | Onion |
| 7 | L-Carvone | 2 | 0 | 1 | 0 | 3 | Slight onion |
| 8 | L-Menthol | 1 | 0 | 2 | 0 | 3 | Onion |

Mint *Spicata* Terpeneless SX, Mint *Piperita* Cascade SX and Peppermint oil mixture are effective for reducing sulfur malodor and met success criteria with the cumulative sulfur score of 2 or lower. It is noted that for such materials, at the wet and rinse stage, there is sulfur malodor reduction.

Perfume Examples with Sulfur Malodor Reduction Materials

The following are non-limiting examples of perfumes incorporating sulfur malodor reduction materials.

Perfume Example 1: Comparative Perfume Example 1

| CAS | Material Name | Wt % | MORV |
|---|---|---|---|
| 89-43-0 | Methyl 2-[(7-hydroxy-3,7-dimethyloctylidene)amino]benzoate | 0.60 | 2.76 |
| 27606-09-3 | 2,4-Dimethyl-4,4a,5,9b-tetrahydro-2H-indeno[1,2-d][1,3]dioxine | 16.00 | 2.34 |
| 7775-00-0 | 3-[4-(Propan-2-yl)phenyl]propanal | 3.00 | 1.46 |
| 488-10-8 | 3-Methyl-2-[(2Z)-pent-2-en-1-yl]cyclopent-2-en-1-one | 0.60 | 0.92 |
| 65405-77-8 | (3Z)-Hex-3-en-1-yl 2-hydroxybenzoate | 6.00 | 0.59 |
| 94201-19-1 | 8-Methyl-1-oxaspiro[4.5]decan-2-one | 1.00 | 0.53 |
| 107-75-5 | 7-Hydroxy-3,7-dimethyloctanal | 6.00 | 0.36 |
| 68039-49-6 | 2,4-Dimethylcyclohex-3-ene-1-carbaldehyde | 0.40 | 0.15 |
| 121-33-5 | 4-Hydroxy-3-methoxybenzaldehyde | 0.40 | 0.08 |
| 101-86-0 | 2-Benzylideneoctanal | 39.20 | 0.02 |
| 928-96-1 | (3Z)-Hex-3-en-1-ol | 0.40 | −0.14 |
| 10339-55-6 | (6E)-3,7-Dimethylnona-1,6-dien-3-ol | 17.00 | −0.17 |
| 93-58-3 | Methyl benzoate | 0.40 | −0.26 |
| 120-57-0 | 2H-1,3-Benzodioxole-5-carbaldehyde | 3.00 | −0.84 |
| 140-11-4 | Benzyl acetate | 6.00 | −0.93 |

Perfume Example 2: Inventive Perfume Example 1 (Comparative Perfume Example 1+Sulfur Reduction Material)

| CAS | Material Name | Wt % | MORV |
|---|---|---|---|
| 89-43-0 | Methyl 2-[(7-hydroxy-3,7-dimethyloctylidene)amino]benzoate | 0.60 | 2.76 |
| 27606-09-3 | 2,4-Dimethyl-4,4a,5,9b-tetrahydro-2H-indeno[1,2-d][1,3]dioxine | 16.00 | 2.34 |
| 7775-00-0 | 3-[4-(Propan-2-yl)phenyl]propanal | 3.00 | 1.46 |
| 488-10-8 | 3-Methyl-2-[(2Z)-pent-2-en-1-yl]cyclopent-2-en-1-one | 0.60 | 0.92 |
| 65405-77-8 | (3Z)-Hex-3-en-1-yl 2-hydroxybenzoate | 6.00 | 0.59 |
| 94201-19-1 | 8-Methyl-1-oxaspiro[4.5]decan-2-one | 1.00 | 0.53 |
| 107-75-5 | 7-Hydroxy-3,7-dimethyloctanal | 6.00 | 0.36 |
| 68039-49-6 | 2,4-Dimethylcyclohex-3-ene-1-carbaldehyde | 0.40 | 0.15 |
| 121-33-5 | 4-Hydroxy-3-methoxybenzaldehyde | 0.40 | 0.08 |
| 101-86-0 | 2-Benzylideneoctanal | 39.20 | 0.02 |
| 928-96-1 | (3Z)-Hex-3-en-1-ol | 0.40 | −0.14 |
| 10339-55-6 | (6E)-3,7-Dimethylnona-1,6-dien-3-ol | 16.00 | −0.17 |
| 93-58-3 | Methyl benzoate | 0.40 | −0.26 |

| CAS | Material Name | Wt % | MORV |
|---|---|---|---|
| 120-57-0 | 2H-1,3-Benzodioxole-5-carbaldehyde | 3.00 | −0.84 |
| 140-11-4 | Benzyl acetate | 6.00 | −0.93 |
| 112-45-8 | Undec-10-enal | 1.00 | −0.08 |

Inclusion of undec-10-enal in perfume 2 example for sulfur shampoo example 1 below when compared with the same shampoo using perfume 1 example has reduced the cumulative sulfur score from over 5 to under 2.

Perfume Example 3: Inventive Perfume Example 2 (Comparative Perfume Example 1+Multiple Sulfur Reduction Materials)

| CAS | Material Name | Wt % | MORV |
|---|---|---|---|
| 89-43-0 | Methyl 2-[(7-hydroxy-3,7-dimethyloctylidene)amino]benzoate | 0.60 | 2.76 |
| 27606-09-3 | 2,4-Dimethyl-4,4a,5,9b-tetrahydro-2H-indeno[1,2-d][1,3]dioxine | 16.00 | 2.34 |
| 7775-00-0 | 3-[4-(Propan-2-yl)phenyl]propanal | 3.00 | 1.46 |
| 488-10-8 | 3-Methyl-2-[(2Z)-pent-2-en-1-yl]cyclopent-2-en-1-one | 0.60 | 0.92 |
| 65405-77-8 | (3Z)-Hex-3-en-1-yl 2-hydroxybenzoate | 6.00 | 0.59 |
| 94201-19-1 | 8-Methyl-1-oxaspiro[4.5]decan-2-one | 1.00 | 0.53 |
| 107-75-5 | 7-Hydroxy-3,7-dimethyloctanal | 6.00 | 0.36 |
| 68039-49-6 | 2,4-Dimethylcyclohex-3-ene-1-carbaldehyde | 0.40 | 0.15 |
| 121-33-5 | 4-Hydroxy-3-methoxybenzaldehyde | 0.40 | 0.08 |
| 101-86-0 | 2-Benzylideneoctanal | 39.20 | 0.02 |
| 928-96-1 | (3Z)-Hex-3-en-1-ol | 0.40 | −0.14 |
| 10339-55-6 | (6E)-3,7-Dimethylnona-1,6-dien-3-ol | 15.00 | −0.17 |
| 93-58-3 | Methyl benzoate | 0.40 | −0.26 |
| 120-57-0 | 2H-1,3-Benzodioxole-5-carbaldehyde | 3.00 | −0.84 |
| 140-11-4 | Benzyl acetate | 6.00 | −0.93 |
| 112-45-8 | Undec-10-enal | 0.50 | −0.08 |
| 141-13-9 | 2,6,10-Trimethylundec-9-enal | 0.50 | −0.66 |
| 8014-09-3 | Patchouli oil | 1.00 | |

Inclusion of undec-10-enal, 2,6,10,-trimethylundec-9-enal and patchouli oil in perfume 3 example for sulfur shampoo example 1 below when compared with the same shampoo using perfume 1 example has reduced the cumulative sulfur score from over 5 to under 1.

Perfume Example 4: Inventive Perfume Example 3 (Comparative Perfume Example 1+Multiple Sulfur Reduction Materials)

| CAS | Material Name | Wt % | MORV |
|---|---|---|---|
| 89-43-0 | Methyl 2-[(7-hydroxy-3,7-dimethyloctylidene)amino]benzoate | 0.60 | 2.76 |
| 27606-09-3 | 2,4-Dimethyl-4,4a,5,9b-tetrahydro-2H-indeno[1,2-d][1,3]dioxine | 16.00 | 2.34 |
| 7775-00-0 | 3-[4-(Propan-2-yl)phenyl]propanal | 3.00 | 1.46 |
| 488-10-8 | 3-Methyl-2-[(2Z)-pent-2-en-1-yl]cyclopent-2-en-1-one | 0.60 | 0.92 |
| 65405-77-8 | (3Z)-Hex-3-en-1-yl 2-hydroxybenzoate | 6.00 | 0.59 |
| 94201-19-1 | 8-Methyl-1-oxaspiro[4.5]decan-2-one | 1.00 | 0.53 |
| 107-75-5 | 7-Hydroxy-3,7-dimethyloctanal | 6.00 | 0.36 |
| 68039-49-6 | 2,4-Dimethylcyclohex-3-ene-1-carbaldehyde | 0.40 | 0.15 |
| 121-33-5 | 4-Hydroxy-3-methoxybenzaldehyde | 0.40 | 0.08 |
| 101-86-0 | 2-Benzylideneoctanal | 32.20 | 0.02 |
| 928-96-1 | (3Z)-Hex-3-en-1-ol | 0.40 | −0.14 |
| 10339-55-6 | (6E)-3,7-Dimethylnona-1,6-dien-3-ol | 15.00 | −0.17 |
| 93-58-3 | Methyl benzoate | 0.40 | −0.26 |
| 120-57-0 | 2H-1,3-Benzodioxole-5-carbaldehyde | 3.00 | −0.84 |
| 140-11-4 | Benzyl acetate | 6.00 | −0.93 |
| | Peppermint oil mixture | 5.00 | |
| 111998-18-6 | 6-cyclopentylidene-Hexanal | 2.00 | |

Inclusion of Peppermint oil mixture and 6-cyclopentylidene-Hexanal in perfume example 4 for sulfur shampoo example 1 below when compared with the same shampoo using perfume 1 example has reduced the cumulative sulfur score from over 5 to under 1.

Perfume Example 5: Inventive Perfume Example 4 (Comparative Perfume Example 1+Multiple Sulfur Reduction Materials)

| CAS | Material Name | Wt % | MORV |
| --- | --- | --- | --- |
| 89-43-0 | Methyl 2-[(7-hydroxy-3,7-dimethyloctylidene)amino]benzoate | 0.60 | 2.76 |
| 27606-09-3 | 2,4-Dimethyl-4,4a,5,9b-tetrahydro-2H-indeno[1,2-d][1,3]dioxine | 16.00 | 2.34 |
| 7775-00-0 | 3-[4-(Propan-2-yl)phenyl]propanal | 3.00 | 1.46 |
| 488-10-8 | 3-Methyl-2-[(2Z)-pent-2-en-1-yl]cyclopent-2-en-1-one | 0.60 | 0.92 |
| 65405-77-8 | (3Z)-Hex-3-en-1-yl 2-hydroxybenzoate | 6.00 | 0.59 |
| 94201-19-1 | 8-Methyl-1-oxaspiro[4.5]decan-2-one | 1.00 | 0.53 |
| 107-75-5 | 7-Hydroxy-3,7-dimethyloctanal | 6.00 | 0.36 |
| 68039-49-6 | 2,4-Dimethylcyclohex-3-ene-1-carbaldehyde | 0.40 | 0.15 |
| 121-33-5 | 4-Hydroxy-3-methoxybenzaldehyde | 0.40 | 0.08 |
| 101-86-0 | 2-Benzylideneoctanal | 33.20 | 0.02 |
| 928-96-1 | (3Z)-Hex-3-en-1-ol | 0.40 | −0.14 |
| 10339-55-6 | (6E)-3,7-Dimethylnona-1,6-dien-3-ol | 15.00 | −0.17 |
| 93-58-3 | Methyl benzoate | 0.40 | −0.26 |
| 120-57-0 | 2H-1,3-Benzodioxole-5-carbaldehyde | 3.00 | −0.84 |
| 140-11-4 | Benzyl acetate | 6.00 | −0.93 |
|  | Peppermint oil mixture | 5.00 |  |
| 112-31-2 | Decanal | 1.00 |  |

Inclusion of Peppermint oil mixture and decanal in perfume example 5 for sulfur shampoo example 1 below when compared with the same shampoo using perfume 1 example has reduced the cumulative sulfur score from over 5 to under 1.

Perfume Example 6: Comparative Perfume Example 2

| CAS | Material Name | Wt % | MORV |
| --- | --- | --- | --- |
| 125109-85-5 | 3-[3-(Propan-2-yl)phenyl]butanal | 5.00 | 1.88 |
| 105-95-3 | 1,4-Dioxacycloheptadecane-5,17-dione | 10.80 | 1.27 |
| 1205-17-0 | 3-(2H-1,3-Benzodioxol-5-yl)-2-methylpropanal | 5.00 | 1.07 |
| 488-10-8 | 3-Methyl-2-[(2Z)-pent-2-en-1-yl]cyclopent-2-en-1-one | 0.20 | 0.92 |
| 107-75-5 | 7-Hydroxy-3,7-dimethyloctanal | 8.00 | 0.36 |
| 39255-32-8 | Ethyl 2-methylpentanoate | 0.50 | 0.23 |
| 101-86-0 | 2-Benzylideneoctanal | 20.00 | 0.02 |
| 81782-77-6 | 4-Methyldec-3-en-5-ol | 20.00 | −0.11 |
| 928-96-1 | (3Z)-Hex-3-en-1-ol | 0.50 | −0.14 |
| 20126-76-5 | 2-(4-Methylcyclohex-3-en-1-yl)propan-2-ol | 2.00 | −0.17 |
| 10339-55-6 | (6E)-3,7-Dimethylnona-1,6-dien-3-ol | 18.00 | −0.17 |
| 3681-71-8 | (3Z)-Hex-3-en-1-yl acetate | 0.50 | −0.65 |
| 142-92-7 | Hexyl acetate | 1.00 | −1.53 |
| 106-24-1 | (2E)-3,7-Dimethylocta-2,6-dien-1-ol | 5.50 | −1.80 |
| 51685-40-6 | 3,7-Dimethylocta-1,6-dien-3-yl acetate | 3.00 | −2.07 |

Perfume Example 7: Inventive Perfume Example 5
(Comparative Perfume Example 2+Sulfur
Reduction Material)

| CAS | Material Name | Wt % | MORV |
|---|---|---|---|
| 125109-85-5 | 3-[3-(Propan-2-yl)phenyl]butanal | 5.00 | 1.88 |
| 105-95-3 | 1,4-Dioxacycloheptadecane-5,17-dione | 10.80 | 1.27 |
| 1205-17-0 | 3-(2H-1,3-Benzodioxol-5-yl)-2-methylpropanal | 5.00 | 1.07 |
| 488-10-8 | 3-Methyl-2-[(2Z)-pent-2-en-1-yl]cyclopent-2-en-1-one | 0.20 | 0.92 |
| 107-75-5 | 7-Hydroxy-3,7-dimethyloctanal | 8.00 | 0.36 |
| 39255-32-8 | Ethyl 2-methylpentanoate | 0.50 | 0.23 |
| 101-86-0 | 2-Benzylideneoctanal | 19.50 | 0.02 |
| 81782-77-6 | 4-Methyldec-3-en-5-ol | 20.00 | −0.11 |
| 928-96-1 | (3Z)-Hex-3-en-1-ol | 0.50 | −0.14 |
| 20126-76-5 | 2-(4-Methylcyclohex-3-en-1-yl)propan-2-ol | 2.00 | −0.17 |
| 10339-55-6 | (6E)-3,7-Dimethylnona-1,6-dien-3-ol | 18.00 | −0.17 |
| 3681-71-8 | (3Z)-Hex-3-en-1-yl acetate | 0.50 | −0.65 |
| 142-92-7 | Hexyl acetate | 1.00 | −1.53 |
| 106-24-1 | (2E)-3,7-Dimethylocta-2,6-dien-1-ol | 5.50 | −1.80 |
| 51685-40-6 | 3,7-Dimethylocta-1,6-dien-3-yl acetate | 3.00 | −2.07 |
| 300371-33-9 | 3-(3,3-dimethyl-12-dihydroinden-5-yl)propanal | 0.50 | 2.20 |

Inclusion of 3-(3,3-dimethyl-12-dihydroinden-5-yl)propanal in perfume 5 example for sulfur shampoo example 1 below when compared with the same shampoo using perfume 4 example has reduced the cumulative sulfur score from over 5 to under 2.

Perfume Example 8: Inventive Perfume Example 6
(Comparative Perfume Example 2+Multiple Sulfur
Reduction Materials)

| CAS | Material Name | Wt % | MORV |
|---|---|---|---|
| 125109-85-5 | 3-[3-(Propan-2-yl)phenyl]butanal | 5.00 | 1.88 |
| 105-95-3 | 1,4-Dioxacycloheptadecane-5,17-dione | 10.80 | 1.27 |
| 1205-17-0 | 3-(2H-1,3-Benzodioxol-5-yl)-2-methylpropanal | 5.00 | 1.07 |
| 488-10-8 | 3-Methyl-2-[(2Z)-pent-2-en-1-yl]cyclopent-2-en-1-one | 0.20 | 0.92 |
| 107-75-5 | 7-Hydroxy-3,7-dimethyloctanal | 8.00 | 0.36 |
| 39255-32-8 | Ethyl 2-methylpentanoate | 0.50 | 0.23 |
| 101-86-0 | 2-Benzylideneoctanal | 18.00 | 0.02 |
| 81782-77-6 | 4-Methyldec-3-en-5-ol | 20.00 | −0.11 |
| 928-96-1 | (3Z)-Hex-3-en-1-ol | 0.50 | −0.14 |
| 20126-76-5 | 2-(4-Methylcyclohex-3-en-1-yl)propan-2-ol | 2.00 | −0.17 |
| 10339-55-6 | (6E)-3,7-Dimethylnona-1,6-dien-3-ol | 18.00 | −0.17 |
| 3681-71-8 | (3Z)-Hex-3-en-1-yl acetate | 0.50 | −0.65 |
| 142-92-7 | Hexyl acetate | 1.00 | −1.53 |
| 106-24-1 | (2E)-3,7-Dimethylocta-2,6-dien-1-ol | 5.50 | −1.80 |
| 51685-40-6 | 3,7-Dimethylocta-1,6-dien-3-yl acetate | 3.00 | −2.07 |
| 300371-33-9 | 3-(3,3-dimethyl-12-dihydroinden-5-yl)propanal | 0.50 | 2.20 |
| 112-45-8 | Undec-10-enal | 0.50 | −0.08 |
| 112-31-2 | Decanal | 0.50 | −0.44 |
| 141-13-9 | 2,6,10-Trimethylundec-9-enal | 0.50 | −0.66 |

Inclusion of 3-(3,3-dimethyl-12-dihydroinden-5-yl)propanal, undec-10-enal, decanal, and 2,6,10,-trimethylundec-9-enal in perfume 6 example for sulfur shampoo example 1 below when compared with the same shampoo using perfume 4 example has reduced the cumulative sulfur score from over 5 to under 1.

Perfume example 9: Inventive perfume example 7 (comparative perfume example 2+sulfur reduction material):

| CAS | Material Name | Wt % | MORV |
|---|---|---|---|
| 125109-85-5 | 3-[3-(Propan-2-yl)phenyl]butanal | 5.00 | 1.88 |
| 105-95-3 | 1,4-Dioxacycloheptadecane-5,17-dione | 10.80 | 1.27 |
| 1205-17-0 | 3-(2H-1,3-Benzodioxol-5-yl)-2-methylpropanal | 5.00 | 1.07 |
| 488-10-8 | 3-Methyl-2-[(2Z)-pent-2-en-1-yl]cyclopent-2-en-1-one | 0.20 | 0.92 |
| 107-75-5 | 7-Hydroxy-3,7-dimethyloctanal | 8.00 | 0.36 |
| 39255-32-8 | Ethyl 2-methylpentanoate | 0.50 | 0.23 |
| 101-86-0 | 2-Benzylideneoctanal | 18.00 | 0.02 |
| 81782-77-6 | 4-Methyldec-3-en-5-ol | 20.00 | −0.11 |

-continued

| CAS | Material Name | Wt % | MORV |
|---|---|---|---|
| 928-96-1 | (3Z)-Hex-3-en-1-ol | 0.50 | −0.14 |
| 20126-76-5 | 2-(4-Methylcyclohex-3-en-1-yl)propan-2-ol | 2.00 | −0.17 |
| 10339-55-6 | (6E)-3,7-Dimethylnona-1,6-dien-3-ol | 18.00 | −0.17 |
| 3681-71-8 | (3Z)-Hex-3-en-1-yl acetate | 0.50 | −0.65 |
| 142-92-7 | Hexyl acetate | 1.00 | −1.53 |
| 106-24-1 | (2E)-3,7-Dimethylocta-2,6-dien-1-ol | 5.50 | −1.80 |
| 51685-40-6 | 3,7-Dimethylocta-1,6-dien-3-yl acetate | 3.00 | −2.07 |
| 70788-30-6 | Cyclohexanepropanol, 2,2,6-trimethyl-α-propyl- | 2.00 | |

Inclusion of Cyclohexanepropanol, 2,2,6-trimethyl-α-propyl—in perfume example 9 for sulfur shampoo example 1 below when compared with the same shampoo using perfume 6 example has reduced the cumulative sulfur score from over 5 to under 1.

Perfume Example 10: Inventive Perfume Example 8 (Comparative Perfume Example 2+Multiple Sulfur Reduction Materials)

| CAS | Material Name | Wt % | MORV |
|---|---|---|---|
| 125109-85-5 | 3-[3-(Propan-2-yl)phenyl]butanal | 5.00 | 1.88 |
| 105-95-3 | 1,4-Dioxacycloheptadecane-5,17-dione | 10.80 | 1.27 |
| 1205-17-0 | 3-(2H-1,3-Benzodioxol-5-yl)-2-methylpropanal | 5.00 | 1.07 |
| 488-10-8 | 3-Methyl-2-[(2Z)-pent-2-en-1-yl]cyclopent-2-en-1-one | 0.20 | 0.92 |
| 107-75-5 | 7-Hydroxy-3,7-dimethyloctanal | 8.00 | 0.36 |
| 39255-32-8 | Ethyl 2-methylpentanoate | 0.50 | 0.23 |
| 101-86-0 | 2-Benzylideneoctanal | 18.00 | 0.02 |
| 81782-77-6 | 4-Methyldec-3-en-5-ol | 20.00 | −0.11 |
| 928-96-1 | (3Z)-Hex-3-en-1-ol | 0.50 | −0.14 |
| 20126-76-5 | 2-(4-Methylcyclohex-3-en-1-yl)propan-2-ol | 2.00 | −0.17 |
| 10339-55-6 | (6E)-3,7-Dimethylnona-1,6-dien-3-ol | 18.00 | −0.17 |
| 3681-71-8 | (3Z)-Hex-3-en-1-yl acetate | 0.50 | −0.65 |
| 142-92-7 | Hexyl acetate | 1.00 | −1.53 |
| 106-24-1 | (2E)-3,7-Dimethylocta-2,6-dien-1-ol | 5.50 | −1.80 |
| 51685-40-6 | 3,7-Dimethylocta-1,6-dien-3-yl acetate | 3.00 | −2.07 |
| 70788-30-6 | Cyclohexanepropanol, 2,2,6-trimethyl-α-propyl- | 1.00 | |
| 111998-18-6 | 6-cyclopentylidene-Hexanal | 1.00 | |

Inclusion of Cyclohexanepropanol, 2,2,6-trimethyl-α-propyl- and 6-cyclopentylidene-Hexanal in perfume example 10 for sulfur shampoo example 1 below when compared with the same shampoo using perfume example 6 has reduced the cumulative sulfur score from over 5 to under 1.

Shampoo with Malodor Reducing Composition

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

Shampoo Examples

| Ingredients | Example 1 | Example 2 | Example 3 | Example 4 | Example 4 | Example 6 | Example 7 | Example 8 |
|---|---|---|---|---|---|---|---|---|
| Sodium Laureth-1 Sulfate [1] | 5.20 | 5.00 | 10.50 | 5.20 | 7.00 | 7.00 | 7.00 | 7.00 |
| Sodium Lauryl Sulfate [2] | 6.80 | 7.00 | 1.50 | 6.80 | 5.00 | 5.00 | 5.00 | 5.00 |
| Cocamidopropyl Betaine [3] | 1.00 | 1.00 | 1.00 | 1.00 | 1.00 | 1.00 | 1.00 | 1.00 |
| Cocamide MEA [4] | 1.00 | 1.00 | 1.00 | — | 1.00 | 1.00 | 1.00 | 1.00 |
| Sulfur [5] | 2.00 | 5.00 | 5.00 | 3.50 | 5.00 | 2.00 | 2 | 2 |
| Acrylates Copolymer [6] | 0.50 | 0.75 | 1.00 | 0.75 | 1.00 | 0.75 | — | 0.6 |
| Guar Hydroxypropyltrimonium Chloride [7] | 0.30 | 0.20 | — | — | — | 0.40 | — | 0.30 |

-continued

| Ingredients | Example 1 | Example 2 | Example 3 | Example 4 | Example 4 | Example 6 | Example 7 | Example 8 |
|---|---|---|---|---|---|---|---|---|
| Guar Hydroxypropyl-trimonium Chloride[8] | — | — | 0.40 | 0.30 | 0.40 | — | 0.2 | — |
| Polyquaternium-76 [9] | 0.01 | 0.10 | — | — | — | 0.15 | 0.01 | — |
| Dimethicone [10] | 0.80 | 1.20 | 1.25 | 1.00 | 1.00 | 2.00 | 1.00 | 1.00 |
| Glycol Distearate [11] | 2.50 | 1.00 | 1.00 | — | — | 1.00 | 4.0 | 2.5 |
| Trihydroxystearin [12] | — | — | — | 0.30 | 0.30 | — | — | — |
| Sodium Benzoate [13] | 0.25 | 0.25 | 0.25 | 0.25 | 0.25 | 0.25 | 0.25 | 0.25 |
| Methylchloroisothiazolinone/ Methylisothiazolinone [14] | 0.05 | 0.05 | 0.05 | 0.05 | 0.05 | 0.05 | 0.05 | 0.05 |
| Sodium Hydroxide [15] | QS | QS | QS | QS | QS | QS | QS | QS |
| Citric Acid [16] | QS | QS | QS | QS | QS | QS | QS | QS |
| Hydrochloric acid [17] | QS | QS | QS | QS | QS | QS | QS | QS |
| Sodium Chloide [18] | QS | QS | QS | QS | QS | QS | QS | QS |
| Sodium Xylene Sulfonate [19] | QS | QS | QS | QS | QS | QS | QS | QS |
| Salicylic Acid [20] | — | — | 3.00 | — | — | 1.8 | — | — |
| Water | QS | QS | QS | QS | QS | QS | QS | QS |
| Neat Fragrance | 1.00 | 1.20 | 1.00 | 1.00 | 0.85 | 1.00 | 1.2 | 1.2 |
| Malodor Reducing Composition | 0.25 | 0.25 | 0.175 | 0.175 | 0.175 | 0.175 | 0.25 | 0.25 |

[1] Sodium Laureth-1 Sulfate at 26% active, supplier: P&G
[2] Sodium Lauryl Sulfate at 29% active, supplier: P&G
[3] Tego Betain L 7 OK at 30% active, supplier: Evonik
[4] Ninol Comf at 85% active, supplier: Stepan
[5] Sulfar, supplier: Vertellus
[6] Carbopol Aqua SF-1 at 30% active, supplier: Lubrizol
[7] Jaguar C-500, supplier: Solvay
[8] N-Hance BF-17, supplier: Ashland Specialty Ingredients
[9] Mirapol AT-1 at 10% active, supplier: Solvay
[10] CF330M, supplier: Momentive
[11] TEGIN G 1100, supplier: Evonik
[12] Thixcin R, Supplier Elementis
[13] Sodium Benzoate Dense NF/FCC, supplier: Emerald Performance Materials
[14] Kathon CG at 1.5% active, supplier: Dow
[15] Sodium Hydroxide—Caustic Soda at 50% active, supplier: K.A. Steel Chemicals, Inc.; level adjustable as process aid or to achieve target pH
[16] Citric Acid Anhydrous, supplier: Archer Daniels Midland; level adjustable to achieve target pH
[17] 6N HCl, supplier: J.T. Baker, level adjustable to achieve target pH
[18] Sodium Chloride, supplier: Morton; level adjustable to achieve target viscosity
[19] Stepanate SXS at 40%, supplier: Stepan
[20] Salicylic Acid, supplier: Salicylates and Chemicals Rinse Out Conditioner Examples The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

| Components | Ex.9 | Ex.10 | Ex.11 | Ex.12 | Ex.13 |
|---|---|---|---|---|---|
| Polyquaternium-6 *1 | 0.075 | — | — | — | — |
| Polyquaternium-6 *2 | — | 0.075 | 0.075 | 0.075 | 0.075 |
| Selenium Disulfide *5 | 1.0 | 0.5 | — | — | — |
| Sulfur *6 | — | — | 2.0 | 2.0– | 5.0 |
| Stearamidopropyl-dimethylamine | 2.0 | — | — | — | — |
| l-glutamic acid | 0.64 | — | — | — | — |
| Behenyl trimethyl ammonium methosulfate | — | 1.8 | 1.8 | 1.8 | 1.8 |
| Dicetyl dimethyl ammonium chloride | — | 0.52 | 0.52 | 0.52 | 0.52 |
| Cetyl alcohol | 2.5 | 1.1 | 1.1 | 1.1 | 1.1 |
| Stearyl alcohol | 4.5 | 2.75 | 2.75 | 2.75 | 2.75 |
| Polydimethylsiloxane *7 | 0.6 | — | — | — | — |
| Aminosilicone *8 | — | 0.75 | 0.75 | 0.75 | 0.75 |
| Preservatives | 0.45 | 0.4 | 0.4 | 0.4 | 0.4 |
| Perfume | 0.5 | 0.5 | 0.5 | 0.5 | 0.5 |
| Malodor Reducing Composition | 0.125 | 0.1 | 0.25 | 0.175 | — |

-continued

| Components | Ex.9 | Ex.10 | Ex.11 | Ex.12 | Ex.13 |
|---|---|---|---|---|---|
| Deionized Water | | | q.s. to 100% | | |
| Method of preparation | I | II | I | II | I |

*1 Polyquaternium-6: Poly(diallyldimethylammonium chloride) supplied with a tradename Merquat 100 from Lubrizol, having a charge density of about 6.2 meq/g, and molecular weight of about 150,000 g/mol
*2 Polyquaternium-6: Poly(diallyldimethylammonium chloride) supplied with a tradename Merquat 106 from Lubrizol having a charge density of about 6.2 meq/g, and molecular weight of about 15,000 g/mol
*5 Selenium Disulfide, from Eskay
*6 Sulfur, from Vertellus
*7 Polydimethylsiloxane: having a viscosity of 10,000 cSt
*8 Aminosilicone: Terminal aminosilicone which is available from GE having a viscosity of about 10,000 mPa · s, and having following formula: $(R_1)_a G_{3-a}-Si-(-OSiG_2)_n-O-SiG_{3-a}(R_1)_a$ wherein G is methyl; a is an integer of 1; n is a number from 400 to about 600; $R_1$ is a monovalent radical conforming to the general formula $C_q H_{2q} L$, wherein q is an integer of 3 and L is $-NH_2$.

| Components | Ex. 14 | Ex. 15 | Ex. 16 |
|---|---|---|---|
| Polyquaternium-6 *1 | — | — | — |
| Polyquaternium-6 *2 | 0.075 | 0.075 | 0.075 |
| Zinc pyrithione *3 | 0.75 | 0.75 | 0.75 |
| Zinc carbonate *4 | 1.6 | 1.6 | 1.6 |
| Selenium Disulfide *5 | | | |
| Sulfur *6 | 3.5 | 2.0 | 2.0 |
| Stearamidopropyl-dimethylamine | — | — | — |
| l-glutamic acid | — | — | — |
| Behenyl trimethyl ammonium methosulfate | 1.8 | 1.8 | 1.8 |
| Dicetyl dimethyl ammonium chloride | 0.52 | 0.52 | 0.52 |
| Cetyl alcohol | 1.1 | 1.1 | 1.1 |
| Stearyl alcohol | 2.75 | 2.75 | 2.75 |
| Polydimethylsiloxane *7 | — | — | — |
| Aminosilicone *8 | 0.75 | 0.75 | 0.75 |
| Preservatives | 0.4 | 0.4 | 0.4 |
| Perfume | 0.5 | 0.5 | 0.5 |
| Malodor Reducing Composition | 0.175 | 0.25 | 0.25 |
| Deionized Water | | QS to 100% | |
| Method of preparation | II | II | II |

*1 Polyquaternium-6: Poly(diallyldimethylammonium chloride) supplied with a tradename Merquat 100 from Lubrizol, having a charge density of about 6.2 meq/g, and molecular weight of about 150,000 g/mol
*2 Polyquaternium-6: Poly(diallyldimethylammonium chloride) supplied with a tradename Merquat 106 from Lubrizol having a charge density of about 6.2 meq/g, and molecular weight of about 15,000 g/mol
*5 Selenium Disulfide, from Eskay
*6 Sulfur, from Vertellus
*7 Polydimethylsiloxane: having a viscosity of 10,000 cSt
*8 Aminosilicone: Terminal aminosilicone which is available from GE having a viscosity of about 10,000 mPa · s, and having following formula: $(R_1)_a G_{3-a}-Si-(-OSiG_2)_n-O-SiG_{3-a}(R_1)_a$ wherein G is methyl; a is an integer of 1; n is a number from 400 to about 600; $R_1$ is a monovalent radical conforming to the general formula $C_q H_{2q} L$, wherein q is an integer of 3 and L is $-NH_2$.

Method of Preparation

The conditioning compositions of "Ex. 1" through "Ex.3" and "CEx. i as shown above can be prepared by any conventional method well known in the art. They are suitably made by one of the following Methods I or II as shown above.

Method I

Cationic surfactants and high melting point fatty compounds are added to water with agitation, and heated to about 80° C. The mixture is cooled down to about 55° C. and gel matrix is formed. Sulfur or selenium sulfide, and if included, silicones and preservatives, are added to the gel matrix with agitation. Then, and if included, polymers are added with agitation at about 45° C. Then, if included, other components such as perfumes are added with agitation. Then the composition is cooled down to room temperature.

Method II

Cationic surfactants and high melting point fatty compounds are mixed and heated to from about 66° C. to about 85° C. to form an oil phase. Separately, water is heated to from about 20° C. to about 48° C. to form an aqueous phase. In Becomix® direct injection rotor-stator homogenizer, the oil phase is injected and it takes 0.2 second or less for the oils phase to reach to a high shear field having an energy density of from $1.0 \times 10^5$ $J/m^3$ to $1.0 \times 10^7$ $J/m^3$ where the aqueous phase is already present. A gel matrix is formed at a temperature of above 50° C. to about 60° C. Silicones, Perfume, Polymer and Preservative, if included, are added to the gel matrix with agitation at temperature below 55° C. and mixed well. Then, selenium sulfide or sulfur, are added to the gel matrix with agitation at temperature below 50° C. and mix well.

Finally the composition is cooled down to room temperature.

Leave on Treatment Formulations and Examples

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

| | Example 17 Active wt % | Example 18 Active wt % | Example 19 Active wt % | Example 20 Active wt % | Example 21 Active wt % | Example 22 Active wt % |
|---|---|---|---|---|---|---|
| Water | Q.S. | Q.S. | Q.S. | Q.S. | Q.S. | Q.S. |
| Alcohol 100% (Ethanol) | 50 | — | 50 | — | 50 | — |
| Acrylates/C10-30 alkyl acrylate crosspolymer[1] | 0.35 | 0.2 | 0.35 | 0.2 | 0.35 | 0.2 |
| Selenium Sulfide[2] | 0.1 | 0.1 | — | — | — | — |

-continued

|  | Example 17 Active wt % | Example 18 Active wt % | Example 19 Active wt % | Example 20 Active wt % | Example 21 Active wt % | Example 22 Active wt % |
|---|---|---|---|---|---|---|
| Sulfur[3] | — | — | 2.0 | 2.0 | 2.0 | 2.0 |
| Panthenol[4] | 0.15 |  | 0.15 |  | 0.15 | 0.1 |
| Niacinamide[5] | 2.5 | 2.5 | 2.5 | 2.5 | 2.5 | 2.5 |
| Caffeine[6] | 0.75 | 0.75 | 0.75 | 0 | 0.75 | 0 |
| Glycerin[7] | 0.5 | 0.5 | 0.5 | 0.5 | 0.5 | 0 |
| Propylene Glycol[8] | 0 | 0.9 | 0 | 1.0 | 0 | 1.0 |
| Menthol[9] | 0.30 | 0.0 | 0.30 | 0.1 | 0.30 | 0.0 |
| Benzyl Alcohol[10] |  | 0.4 |  | 0.4 |  | 0.4 |
| Methyliso-thiazolinone[11] | 0 | 0.05 | 0 | 0.05 | 0 | 0.05 |
| PEG-40 Hydrogenated Castor Oil[12] | 0 | 0.5 | 0 | 0.5 | 0 | 0.5 |
| Tetrahydroxy-propyl Ethylene-diamine[13] | 0.12 | 0.14 | 0.12 | 0.14 | 0.12 | 0.14 |
| Fragrance | 0.4 | 0.2 | 0.4 | 0.2 | 0.4 | 0.2 |
| Malodor Reducing Composition | 0.15 | 0.1 | 0.15 | 0.1 | 0.15 | 0.1 |

[1]Carbopol Ultrez 21 available from Lubrizol
[2]Selenium sulfide from Eskay
[3]Sulfur from Vertellus
[4]D-Panthenol from BASF
[5]Niacinamide from Lonza
[6]Caffeine from Merck
[7]Glycerin from Procter & Gamble
8Propylene Glycol from Sigma Aldrich
[9]Menthol from Kerry Ingredients and Flavors
[10]Benzyl Alcohol, NF from Charkit
[11]Kathon CG at 1.5% active from Dow
[12]Cremophor RH 40 from BASF
[13]Neutrol Te from BASF In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition Combinations Paragraph A. A hair care composition comprising, based on total composition weight,
a) a sum total of from about 0.1% to about 2% of a perfume with one or more malodor reduction materials having a wt % from about 0.0001% to about 2% of one or more of said malodor reduction materials wherein the malodor reduction material is selected from the group consisting of 2'-isopropyl-1,7,7-trimethylspiro[bicyclo[2.2.1]heptane-2,4'-[1,3]dioxane], (1',1',5',5'-tetramethylhexahydro-2'H,5'H-spiro[[1,3]dioxolane-2,8'-[2,4a]methanonaphthalene], 3a,4,5,6,7,7a-hexahydro-1H-4,7-methanoinden-6-yl acetate), Decahydro-3H-spiro[furan-2,5'-[4,7]methanoindene], CEDRYL METHYL ETHER, Ethyl (1R,2R,3R,4R)-3-isopropylbicyclo[2.2.1]hept-5-ene-2-carboxylate, 3aR,5aR,9aR,9bR)-3a,6,6,9a-tetramethyldodecahydronaphtho[2,1-b]furan, alpha, alpha,6,6-tetramethyl bicyclo[3.1.1]hept-2-ene-propanal, 4,5-epoxy-4,11,11-trimethyl-8-methylenebicyclo(7.2.0)undecane), 4aR,8aS)-7-methyloctahydro-1,4-methanonaphthalen-6(2H)-one, 5-methoxyoctahydro-1H-4,7-methanoindene-2-carbaldehyde, 8,8-dimethyl-6,7-dihydro-5H-naphthalene-2-carbaldehyde, 2R,4a' R,8a' R)-3,7'-dimethyl-3',4',4a',5',8',8a'-hexahydro-1'H-spiro[oxirane-2,2'-[1,4]methanonaphthalene]), (2,2,6,6,7,8,8-heptamethyldecahydro-2H-indeno[4,5-b]furan, 1,3,4,6,7,8alpha-hexahydro-1,1,5,5-tetramethyl-2H-2,4alpha-methanophtalen-8(5H)-one), 3a,4,5,6,7,7a-hexahydro-1H-4,7-methanoinden-5-yl isobutyrate, 3S,5aR,7aS,11aS,11bR)-3,8,8,11a-tetramethyl-dodecahydro-5H-3,5a-epoxynaphtho[2,1-c]oxepine, (8,8-dimethyl-3a,4,5,6,7,7a-hexahydro-1H-4,7-methanoinden-6-yl propionate), 4aR,5R,7aS,9R)-2,2,5,8,8,9a-hexamethyloctahydro-4H-4a,9-methanoazuleno[5,6-d][1,3]dioxole, 2-(8-isopropyl-6-methylbicyclo[2.2.2]oct-5-en-2-yl)-1,3-dioxolane, 3a,4,5,6,7,7a-hexahydro-1H-4,7-methanoinden-6-yl pivalate, 3a,5,6,7,8,8b-hexahydro-2,2,6,6,7,8,8-heptamethyl-4H-indeno (4,5-d)-1,3-dioxole, (3R-(3 alpha, 3a,6alpha,7,8aalpha))-octahydro-3,6,8,8-tetramethyl-1H-3a,7-methanoazulen-6-yl formate, (1S,2R,5S,7R,8R)-2,6,6,8-tetramethyltricyclo[5.3.1.01.5]undecan-8-ol, 1-((2S,3 S)-2,3,8,8-tetramethyl-1,2,3,4,5,6,7,8-octahydronaphthalen-2-yl)ethan-1-one, ((E)-4-((3aS,7aS)-octahydro-5H-4,7-methanoinden-5-ylidene)butanal, 1R-(1alpha,4beta, 4aalpha,6beta,8aalpha))-octahydro-4,8a,9,9-tetramethyl-1,6-methano-1(2H)-naphthol, [(3Z)-4,11,11-trimethyl-8-methylidene-5-bicyclo[7.2.0]undec-3-enyl]acetate, (1aR, 4S,4aS,7R,7aS,7bS)-1,1,4,7-tetramethyldecahydro-1H-cyclopropa[e]azulen-4-ol, Z)-6-ethylideneoctahydro-2H-5, 8-methanochromen-2-one), 1-((3R,3aR,7R,8aS)-3,6,8,8-tetramethyl-2,3,4,7,8,8a-hexahydro-1H-3a,7-methanoazulen-5-yl)ethan-1-one, 3,5,5,6,7,8,8-heptamethyl-5,6,7,8-tetrahydronaphthalene-2-carbonitrile, 4-(1,7,7-trimethyl-6-bicyclo[2.2.1]heptanyl)cyclohexan-1-ol, (E)-4-((3aR,4R,7R,7aR)-1,3a,4,6,7,7a-hexahydro-5H-4,7-methanoinden-5-ylidene)-3-methylbutan-2-ol, (E)-3,7-dimethylocta-2,6-dien-1-yl palmitate), 1,3,4,6,7,8-hexahydro-4,6,6,7,8,8,-hexamethylcyclopenta[g]benzopyran, 5H-Cyclopenta quinazoline,6,6a,7,8,9,9a-hexahydro-7,7,8,9,9-pentamethyl-, Cyclopentaneacetic acid, 3-oxo-2-pentyl-, methyl ester, Cyclohexanol, 3-(5,5,6-trimethylbicyclo[2.2.1]hept-2-yl)-, Cyclopentanecarboxylic acid, 2-hexyl-3-oxo-, methyl ester, Naphtho[2,1b]furan, dodecahydro-3a,6,6,9a-tetramethyl-, (3aR,5aS,9aS,9bR)—, Ethanone, 1-(1,2,3,5,6,7,8,8a-octahydro-2,3,8,8-tetramethyl-2-naphthalenyl)-, Ethanone, 1-(1,2,3,4,6,7,8,8a-octahydro-2,3,8,8-tetramethyl-2-naphthalenyl)-, 2-Naphthalenecarboxald ehyde, 1,2,3,4,5,6,7,8-octahydro-8,8-dimethyl-, 1H-3a,7-Methanoazulen-6-ol, octahydro-3,6,8,8-tetramethyl-, 6-acetate, (3R,3aS,6R,7R,8aS)-, Tricyclo [6.3.1.02.5]dodecan-1-ol, 4,4,8-trimethyl-, (1R,2S,5R,8S)—, 1H-3a,6-Methanoazulene-3-methanol, octahydro-7,7-dimethyl-8-methylene-, (3S,3aR,6R,8aS)-, 1H-Indole-1-heptanol, η-1H-indol-1-yl-α,α,ε-trimethyl-, Decanal, undec-10-enal, 6-cyclopentylidene-Hexanal, 2,6,10-Trimethylundec-9-enal, 3-(3,3-dimethyl-12-dihydroinden-5-yl) propanal, 4-Dodecenal, Dec-4-enal, [(1R2S)-1-methyl-2-[[(1R3S5S)-122-trimethyl-3-bicyclo[3.1.0]hexanyl]methyl] cyclopropyl]methanol, 1-Naphthalenol, 1,2,3,4,4a, 7,8,8a-octahydro-2,4a,5,8a-tetramethyl-, 1-formate, Cyclohexanepropanol, 2,2,6-trimethyl-α-propyl-, Cyclododecaneethanol, β-methyl-, Ethyl cyclohexanecarboxylate, 6-Oxabicyclo[3.2.1]octane, 5-methyl-1-(2,2,3-trimethyl-3-cyclopenten-1-yl)-, Cyclododecane, 1,1-dimethoxy-, 2,6,10-Dodecatrien-1-ol, 3,7,11-trimethyl-, 2-Nonynoic acid, methyl ester, 2,6-Nonadien-1-del, (2E,6Z)-3,6-Nonadien-1-ol, Patchouli and derivatives, Patchouli oil MD, Patchouli Indonesia, Patchouli 30 and Oils, Patchouli, patchoulol synthase-modified *Saccharomyces cerevisiae*-fermented, from carbohydrates sold under the trademark Clear Wood®, Mint *Spicata* Terpeneless SX, Mint *Piperita* Cascade SX, Peppermint oil mixture and mixtures thereof;
  b) from about 0.01% to about 10% of a scalp active material selected from the group consisting of sulfur and mixtures thereof;
  c) from about 0.1% to about 40% of a surfactant.

Paragraph B A hair care composition according to Paragraph A, wherein the malodor reduction material has a sulfur malodor reduction value MORV>3 and a ClogP>3.

Paragraph C A hair care composition according to Paragraph A-B, wherein the malodor reduction material has a sulfur malodor reduction value MORV>3 and ClogP>3 and a VP>0.005.

Paragraph D A hair care composition according to Paragraph A-C, wherein the malodor reduction material is selected from the group consisting of Decanal, undec-10-enal, 6-cyclopentylidene-Hexanal, 2,6,10-Trimethylundec-9-enal, 3-(3,3-dimethyl-12-dihydroinden-5-yl)propanal, 4-Dodecenal, and Dec-4-enal and mixtures thereof.

Paragraph E A hair care composition according to Paragraph A-D, wherein the malodor reduction material is selected from the group consisting of [(1R2S)-1-methyl-2-[[(1R3S5S)-122-trimethyl-3-bicyclo[3.1.0]hexanyl]methyl] cyclopropyl]methanol, 1-Naphthalenol, 1,2,3,4,4a,7,8,8a-octahydro-2,4a,5,8a-tetramethyl-, 1-formate, Cyclohexanepropanol, 2,2,6-trimethyl-α-propyl-, Cyclododecaneethanol, β-methyl-, Ethyl cyclohexanecarboxylate, 6-Oxabicyclo[3.2.1]octane, 5-methyl-1-(2,2,3-trim ethyl-3-cyclopenten-1-yl)-, Cyclododecane, 1,1-dimethoxy-, 2,6,10-Dodecatrien-1-ol, 3,7,11-trimethyl-, 2-Nonynoic acid, methyl ester, 2,6-Nonadien-1-ol, (2E,6Z)-3,6-Nonadien-1-ol and mixtures thereof.

Paragraph F A hair care composition according to Paragraph A-E, wherein the malodor reduction material is selected from the group consisting of Patchouli and derivatives, Patchouli oil MD, Patchouli Indonesia, Patchouli 30, Oils, Patchouli, patchoulol synthase-modified *Saccharomyces cerevisiae*-fermented, from carbohydrates sold under the trademark Clear Wood® and mixtures thereof.

Paragraph G A hair care composition according to Paragraph A-F, wherein the malodor reduction material is selected from the group consisting of Mint *Spicata* Terpeneless SX, Mint *Piperita* Cascade SX, Peppermint oil mixture and mixtures thereof.

Paragraph H A hair care composition according to Paragraph A-G, wherein there is a cumulative sulfur odor of 0 to 2.

Paragraph I A hair care composition according to Paragraph A-H, wherein the surfactant is selected from the group consisting of anionic, amphoteric or zwitterionic, cationic or mixtures thereof.

Paragraph J A hair care composition according to Paragraph A-I, wherein the composition comprises the sum total of from about 0.0001% to about 0.5% of the malodor reduction material.

Paragraph K A hair care composition according to Paragraph A-J, wherein the composition comprises the sum total of from about 0.0002% to about 0.25% of the malodor reduction material.

Paragraph L A hair care composition according to Paragraph A-K, wherein the hair care composition is a shampoo, Paragraph M A hair care composition according to Paragraph A-L, wherein the hair care composition is a rinse off conditioner.

Paragraph N A hair care composition according to Paragraph A-M, wherein the hair care composition is a leave on treatment, Paragraph O A method of controlling malodors according to Paragraph A-N, comprising: contacting a situs comprising a malodor and/or a situs that will become malodorous with a hair care composition selected from the group consisting of the hair care composition of Paragraph A.

Paragraph P The method according to paragraph A-O, wherein, said situs is a head of hair and said contacting step comprises contacting said head of hair with a sufficient amount of a hair care composition to provide said hair with a level of malodor reduction material at least 0.0001 mg of malodor reduction material.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. A hair care composition comprising, based on total composition weight,
    a) a sum total of from about 0.1% to about 2% of a perfume from about 0.00001% to about 2% of malodor reduction materials where in the malodor materials are mixtures of decanal and undec-10-enal and 6-cyclopentylidene-Hexanal and 2,6,10-Trimethylundec-9-enal and 3-(3,3-dimethyl-12-dihydroinden-5-yl)propanal and 4-Dodecenal and Dec-4-enal
    b) from about 0.01% to about 10% of sulfur;
    c) from about 0.1% to about 40% of a surfactant.

2. A hair care composition according to claim 1 wherein the malodor reduction materials have a sulfur malodor reduction value >3 and a C log P>3.

3. A hair care composition according to claim 1 wherein the malodor reduction materials have a sulfur malodor reduction value >3 and C log P>3 and a Vapour Pressure >0.005.

4. A hair care composition according to claim 1 wherein there is a cumulative sulfur odor of 0 to 2.

5. A hair care composition according to claim 1, wherein the surfactant is selected from the group consisting of anionic, amphoteric or zwitterionic, cationic or mixtures thereof.

6. A hair care composition according to claim 1 wherein the composition comprises from about 0.0001% to about 0.5% of the malodor reduction materials.

7. A hair care composition according to claim 1 wherein the composition comprises from about 0.0002% to about 0.25% of the malodor reduction materials.

8. A hair care composition according to claim 1 wherein the hair care composition is a shampoo.

9. A hair care composition according to claim 1 wherein the hair care composition is a rinse off conditioner.

10. A hair care composition according to claim 1 wherein the hair care composition is a leave on treatment.

11. A method of controlling malodors comprising: contacting a the hair with a hair care composition according to claim 1.

* * * * *